(12) United States Patent
Unemori

(10) Patent No.: US 7,553,813 B2
(45) Date of Patent: Jun. 30, 2009

(54) METHODS AND COMPOSITIONS FOR CONTROL OF FETAL GROWTH VIA MODULATION OF RELAXIN

(75) Inventor: Elaine Unemori, Oakland, CA (US)

(73) Assignee: Corthera, Inc., San Mateo, CA (US)

( * ) Notice: Subject to any disclaimer, the term of this patent is extended or adjusted under 35 U.S.C. 154(b) by 0 days.

(21) Appl. No.: 11/120,582

(22) Filed: May 2, 2005

(65) Prior Publication Data

US 2006/0247163 A1 Nov. 2, 2006

Related U.S. Application Data

(60) Provisional application No. 60/567,353, filed on Apr. 30, 2004.

(51) Int. Cl.
*A61K 38/30* (2006.01)

(52) U.S. Cl. .................... 514/12; 435/69.1; 530/399

(58) Field of Classification Search .................. None
See application file for complete search history.

(56) References Cited

U.S. PATENT DOCUMENTS

| | | |
|---|---|---|
| 4,109,496 A | 8/1978 | Alleman et al. |
| 4,215,051 A | 7/1980 | Schroeder et al. |
| 4,267,101 A | 5/1981 | Bigazzi |
| 4,376,110 A | 3/1983 | David et al. |
| 4,683,202 A | 7/1987 | Mullis |
| 4,758,516 A | 7/1988 | Hudson et al. |
| 4,816,397 A | 3/1989 | Boss et al. |
| 4,816,567 A | 3/1989 | Cabilly et al. |
| 4,835,251 A | 5/1989 | Burnier et al. |
| 4,871,670 A | 10/1989 | Hudson et al. |
| 4,873,191 A | 10/1989 | Wagner et al. |
| 4,946,778 A | 8/1990 | Ladner et al. |
| 5,023,321 A | 6/1991 | Hudson et al. |
| 5,075,217 A | 12/1991 | Weber |
| 5,179,195 A | 1/1993 | Hudson et al. |
| 5,225,539 A | 7/1993 | Winter |
| 5,320,953 A | 6/1994 | Hudson et al. |
| 5,326,694 A | 7/1994 | Hudson et al. |
| 5,364,759 A | 11/1994 | Caskey et al. |
| 5,399,349 A | 3/1995 | Paunescu et al. |
| 5,420,111 A | 5/1995 | Gluckman et al. |
| 5,451,572 A | 9/1995 | Cipolla et al. |
| 5,460,959 A | 10/1995 | Mulligan et al. |
| 5,464,756 A | 11/1995 | Henner et al. |
| 5,545,806 A | 8/1996 | Lonberg et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,811,395 A | 9/1998 | Schwabe et al. |
| 5,911,997 A | 6/1999 | Schwabe et al. |
| 5,945,402 A | 8/1999 | Cipolla et al. |
| 5,952,296 A | 9/1999 | Bigazzi |
| 5,972,621 A | 10/1999 | Tartaglia et al. |
| 6,211,147 B1 | 4/2001 | Unemori |
| 6,723,702 B2 | 4/2004 | Conrad et al. |
| 6,780,836 B2 | 8/2004 | Unemori |
| 7,363,076 B2 | 4/2008 | Yun et al. |
| 2002/0123455 A1 | 9/2002 | Ryan et al. |
| 2004/0192606 A1 | 9/2004 | Unemori |
| 2004/0266685 A1 | 12/2004 | Conrad et al. |
| 2005/0026822 A1 | 2/2005 | Tregear et al. |
| 2005/0143299 A1 | 6/2005 | Bigazzi et al. |
| 2005/0153885 A1 | 7/2005 | Yun et al. |
| 2005/0240241 A1 | 10/2005 | Yun et al. |
| 2005/0256028 A1 | 11/2005 | Yun et al. |
| 2006/0034847 A1 | 2/2006 | Yun et al. |
| 2006/0247163 A1 | 11/2006 | Unemori |
| 2006/0247172 A1 | 11/2006 | Unemori |
| 2007/0004619 A1 | 1/2007 | Del Borgo et al. |

FOREIGN PATENT DOCUMENTS

| | | |
|---|---|---|
| EP | 171494 A1 | 2/1986 |
| EP | 173496 A2 | 2/1986 |
| EP | 0407401 B1 | 4/1996 |
| EP | 0845992 B1 | 11/2000 |

(Continued)

OTHER PUBLICATIONS

Hayes et al. "Implantation and pregnancy following In Vitro Fertilization and the effect of recombinant human relaxin administration in *Macaca fascilaris*", 71, Biology of Reproduction, 1591-1597 (2004).*

Ergaz et al. "Intrauterine growth restriction-etiology and consequences: What do we know about the human situation and experimental animal models?", 20, Reproductive Toxicology 301-322 (2005).*

Chen, et al., The pharmacokinetics and absorption of recombinant human relaxin in nonpregnant rabbits and rhesus in non pregnant rabbits and rhesus monkeys after intravenous and intravaginal administration, 1993, Pharmaceutical Research, vol. 10, No. 3, pp. 223-227.*

Gagnon, R. Placental insufficiency and its consequences, 2003, European Journal of Obstetrics and Gynecology and Reproductive Biology, 2003, vol. 110, pp. S99-S107.*

(Continued)

*Primary Examiner*—Manjunath N Rao
*Assistant Examiner*—Ian Dang
(74) *Attorney, Agent, or Firm*—Morrison & Foerster LLP

(57) ABSTRACT

The invention relates to the method for treatment, diagnosis and prevention of diseases related to fetal growth and placental insufficiency and comprises methods including inhibiting or increasing relaxin synthesis, relaxin receptor synthesis, relaxin binding to the relaxin receptor, and relaxin receptor activity. The invention also relates to screening assays to identify compounds that modulate relaxin and/or relaxin receptor activity. The invention further relates to gene therapy methods utilizing relaxin and relaxin-related sequences for the treatment and prevention of diseases related to fetal growth and placental insufficiency.

17 Claims, 4 Drawing Sheets

FOREIGN PATENT DOCUMENTS

| | | |
|---|---|---|
| EP | 1434599 A1 | 4/2003 |
| EP | 1641824 A1 | 12/2004 |
| EP | 1696948 A1 | 7/2005 |
| EP | 1753449 A2 | 12/2005 |
| EP | 0675732 B1 | 6/2006 |
| EP | 1253929 B1 | 5/2007 |
| WO | WO 86/01533 A1 | 3/1986 |
| WO | WO 88/09810 A1 | 12/1988 |
| WO | WO-89/07945 A1 | 9/1989 |
| WO | WO 89/10134 A1 | 11/1989 |
| WO | WO-95/03822 A2 | 2/1995 |
| WO | WO-97/06814 A1 | 2/1997 |
| WO | WO-01/58468 A1 | 8/2001 |
| WO | WO-03/030930 A1 | 4/2003 |
| WO | WO-2004/113381 A1 | 12/2004 |
| WO | WO-2005/060991 A1 | 7/2005 |
| WO | WO-2005/115435 A2 | 12/2005 |

OTHER PUBLICATIONS

Golub et al., Twelve-month evaluation of rhesus monkey dams and infants after relaxin (HRLX-2) infusion in late pregnancy, 1996, Reproductive Toxicology, vol. 10, No. 1, pp. 29-36.*

Adham, et al., "Cloning Of A Cdna For A Novel Insulin-Like Hormone Of The Testicular Leydig Cells," *J. Biol. Chem.* 268:26668-26672 (1993).

Bartsch, et al., "Relaxin Signalling Links Tyrosine Phosphorylation To Phosphodiesterase And Adenylyl Cyclase Activity," *Mol. Hum. Reprod.* 7:799-809 (2001).

Bathgate, et al., "Human Relaxin Gene 3 (H3) and the Equivalent Mouse Relaxin (M3) Gene," *J Biol. Chem.* 277(2):1148-1157 (2002).

Benson and Doubilet "Sonographic Prediction Of Gestational Age: Acccuracy Of Second- And Third-Trimester Fetal Measurements," *AJR Am. J. Roentgenol.* 157:1275-1277 (1991).

Bullesbach and Schwabe, "Specific,.High Affinity Relaxin-like Factor Receptors," *J. Biol. Chem.* 274:22354-22358 (1999).

Chien, et al., "The Two-Hybrid System: A Method To Identify And Clone Genes For Proteins That Interact With A Protein Of Interest," *Proc. Natl. Acad. Sci. USA* 88:9578-9582 (1991).

Cote, et al., "Generation Of Human Monoclonal Antibodies Reactive With Cellular Antigens," *Proc. Natl. Acad. Sci. USA* 80:2026-2030 (1983).

Danielson, et al., "Relaxin Is A Potent Renal Vasodilator In Conscious Rats," *J. Clin. Invest.* 103:525-533 (1999).

Dokras, et al., "Regulation of Human Cytotrophoblast Morphogenesis by Hepatocyte Growth Factor/Scatter Factor," *Biol Reprod.* 65:1278-1288 (2001).

Dschietzig, et al., "Relaxin, a Pregnancy Hormone, Is a Functional Endothelin-1 Antagonist," *Circ. Res.* 92:32-40 (2003).

Frackelton, et al., "Characterization And Use Of Monoclonal Antibodies For Isolation Of Phosphotyrosyl Proteins From Retrovirus-Transformed Cells And Growth Factor-Stimulated Cells," *Mol. Cell. Biol.* 3:1343-1352 (1983).

Greenspan and Bona, "Idiotypes: Structure And Immunogenicity," *FASEB J* 7:437-444 (1993).

Hudson, et al., "Relaxin Gene Expression In Human Ovaries And The Predicted Structure Of A Human Preprorelaxin By Analysis Of cDNA Clones," *Embo. J.* 3(10):2333-2339 (1984).

Huston, et al., "Parathyroid Hormone Modulates Transforming Growth Factor β Activity and Binding in Osteoblast-Enriched Cell Cultures from Fetal Rat Parietal Bone," *Proc, Natl. Acad. Sci. USA* 85:5879-5883 (1988).

Inoue, et al. "Synthesis And Hybridization Studies On Two Complementary Nona(2'-O-Methyl)Ribonucleotides," *Nucl. Acids Res.* 15:6131-6148 (1987).

Inouye and Inouye, "Up-Promoter Mutations In The Lpp Gene Of *Escherichia coli*," *Nucleic Acids Res.* 13:3101-3109 (1985).

Ivell, "Immunoexpression Of The Relaxin Receptor LGR7 In Breast And Uterine Tissues Of Humans And Primates," Reprod *Biol Endocrinol* 1:114 (2003).

Kauma, et al., "Hepatocyte Growth Factor Stimulates Trophoblast Invasion: A Potential Mechanism for Abnormal Placentation in Preeclampsia," *J Clin Endocrinol Metab* 84:4092-4096.

Kumagai, et al., "INSL3/Leydig Insulin-Like Peptide Activates The LGR8 Receptor Important In Testis Descent," *J Biol Chem* 277:31283-31286 (2002).

Lakso, et al., "Targeted Oncogene Activation by Site-Specific Recombination in Transgenic Mice," *Proc. Natl. Acad Sci. USA* 89:6232-6236 (1992).

Lee, et al., "International Small for Gestational Age Advisory Board Consensus Development Conference Statement: Management of Short Children Born Small for Gestational Age," *Pediatrics* 111:1253-1261 (2003).

Lemaitre, et al., "Specific Antiviral Activity of a Poly(L-lysine)-Conjugated Oligodeoxyribonucleotide Sequence Complementary to Vesicular Stomatitis Virus N Protein mRNA Initiation Site," *Proc. Natl. Acad. Sci. USA* 84:648-652 (1987).

Letsinger, et al., "Cholesteryl-Conjugated Oligonucleotides: Synthesis, Properties, and Activity as Inhibitors of Replication of Human Immunodeficiency Virus in Cell Culture," *Proc. Natl. Acad. Sci. USA* 86:6553-6556 (1989).

Liu, et al., "Chimeric Mouse-Human IgGI Antibody that Can Mediate Lysis of Cancer Cells," *Proc. Natl. Acad. Sci. USA* 84:3439-3443 (1987).

Lo, "Transformation By Iontophoretic Microinjection Of DNA: Multiple Integrations Without Tandem Insertions," *Mol Cell Biol* 3:1803-1814 (1983).

Logan and Shenk, "Adenovirus Tripartite Leader Sequence Enhances Translation Of Mrnas Late After Infection," *Proc. Natl. Acad. Sci. USA* 91:3655-3659 (1984).

Mulligan and Berg, "Selection For Animal Cells That Express The *Escherichia coli* Gene Coding For Xanthine-Guanine Phosphoribosyltransferase," *Proc. Natl. Acad. Sci USA* 78:2072-2076 (1981).

O'Hare, et al., "Transformation Of Mouse Fibroblasts To Methotrexate Resistance By A Recombinant Plasmid Expressing A Prokaryotic Dihydrofolate Reductase," *Proc Natl Acad Sci USA* 78:1527 (1981).

Osheroff, et al., "Preparation of biologically active 32P-labeled human relaxin. Displaceable binding to rat uterus, cervix, and brain," *J. Biol. Chem.* 265:9396-9401 (1990).

Osheroff and King, "Binding And Cross-Linking Of 32P-Labeled Human Relaxin To Human Uterine Cells And Primary Rat Atrial Cardiomyocytes," *Endocrinol.* 136:4377-4381 (1995).

Palejwala, et al., "Demonstration Of A Relaxin Receptor And Relaxin-Stimulated Tyrosine Phosphorylation In Human Lower Uterine Segment Fibroblasts," *Endocrinology* 139:1208-1212 (1998).

Parsell, et al., "Relaxin Binds To And Elicits A Response From Cells Of The Human Monocytic Cell LIne, THP-1," *J Biol. Chem.* 271:27936-27941 (1996).

Platt, et al., "Independent Regulation Of Adipose Tissue-Specificity And Obesity Response Of The Adipsin Promoter In Transgenic Mice," *J. Biol. Chem.* 269:28558-28562 (1994).

Ruther, et al., "Easy Identification Of Cdna Clones," *EMBO J.* 2:1791 (1983).

Sambrook, et al., "Molecular Cloning: A Laboratory Manual, Second Edition," Cold Spring Harbor Press, N.Y. (1989).

Sarin, et al., "Inhibition of Acquired Immunodeficiency Syndrome Virus by Oligodeoxynucleoside Methylphosphonates," *Proc. Natl. Acad. Sci. USA* 85:7448-7451 (1988).

Schwabe and Bullebasch,"Relaxin: Structures, Functions, Promises, And Nonevolution," *FASEB J* 8:1152-1160 (1994).

Shirota, et al., "Early Human Preantral Follicles Have Relaxin And Relaxin Receptor (LGR7), And Relaxin Promotes Their Development," *J Clin Endocrinol Metab* 90:516-521 (2005).

Smith, et al., "Molecular Engineering of the Autographa californica Nuclear Polyhedrosis Virus Genome: Deletion Mutations Within the Polyhedrin Gene," *J.Virol.* 46:584-594 (1983).

Stein, et al., "Physicochemical Properties Of Phosphorothioate Oligodeoxynucleotides," *Nucl. Acids. Res.* 16:3209 (1988).

Sun, et al., "Chimeric Antibody with Human Constant Regions and Mouse Variable Regions Directed against Carcinoma-Associated Antigen 17-1A," *Proc. Natl. Acad. Sci. USA* 84:214-218 (1987).

Szybalska and Szybalski, "Genetics of Human Cell Lines, IV. DNA-Mediated Heritable Transformation of a Biochemical Trait ," *Proc Natl Acad Sci USA* 48:2026 (1962).

Tsatsaris, et al., "Overexpression Of The Soluble Vascular Endothelial Growth Factor Receptor In Preeclamptic Patients: Pathophysiological Consequences," *J Clin Endocrinol Metab* 88:5555-5563 (2003).

Unemori, et al., "Relaxin Stimulates Expression Of Vascular Endothelial Growth Factor In Normal Human Endometrial Cells In Vitro And Is Associated With Menometrorrhagia In Women," *Hum. Reprod.* 14:800-806 (1999).

Van der Putten, et al., "Efficient Insertion of Genes into the Mouse Germ Line Via Retroviral Vectors ," *Proc Natl Acad Sci USA* 82:6148-6152 (1985).

Van Heeke and Schuster,"Expression Of Human Asparagine Synthetase In *Escherichia coli*," *J Biol Chem* 264:5503-5509 (1989).

Voller, et al., "Enzyme Immunoassays With Special Reference To ELISA Techniques," *J. Clin. Pathol.* 31:507-520 (1978).

Wagner, et al,"Nucleotide Sequence of the Thymidine Kinase Gene of Herpes Simplex Virus Type 1 ," *Proc. Natl. Acad. Aci. USA* 78:144.1-1445 (1981).

Wigler, et al., "Transformation of Mammalian Cells with an Amplifiable Dominant-Acting Gene," *Proc Natl Acad Sci USA* 77:3567 (1980).

Blair et al., "Optimal Fetal Growth for the Caucasian Singleton and Assessment of Appropriatness of Fetal Growth; and Analyisis of a Total Population Perinatal Database," BMC Pediatrics 5: 13 (2005).

Bathgate, R. A. D. et al. (Jul. 2003). "Relaxin:New Peptides, Receptors and Novel Actions," *Trends in Endocrinology and Metabolism* 14(5):207-213.

Hudson, P. et al. (Feb. 17, 1983). "Structure of a Genomic Clone Encoding Biologically Active Human Relaxin," *Nature* 301:628-631.

International Search Report and Written Opinion mailed on Oct. 12, 2006 for PCT Patent Application No. PCT/US2005/015248 filed on May 2, 2005, 13 pages.

U.S. Office Action mailed on Nov. 28, 2007, for U.S. Appl. No. 11/478,267, filed Jun. 28, 2006, 9 pages.

U.S. Office Action mailed on Sep. 4, 2008, for U.S. Appl. No. 11/478,267, filed Jun. 28, 2006, 12 pages.

U.S. Office Action mailed on Sep. 30, 2008, for U.S. Appl. No. 11/981,338, filed Oct. 31, 2007, 16 pages.

Quattrone et al., "Relaxin potentiates the expression of inducible nitric oxide synthase by endothelial cells from human umbilical vein in in vitro culture," Molecular Human Reproduction 10:325-330 (2004).

Goldsmith, et al., "Relaxin Regulation of Endometrial Structure and Function in the Rhesus Monkey," *PNAS* 101:46985-4689 (2004).

Hayes, et al., "Relaxin Administration During IVF/ET in *Macaca Facicularis*," *Theriogenelogy* 59:365 (2003).

Hayes, et al., "Biology of Primate Relaxin: A Paracrine Signal in Early Pregnancy?" *Reproductive Biology and Endocrinology* 2:1-22 (2004).

Hayes, et al., "Implantation and Pregnancy Following In Vitro Fertilization and the Effect of Recombinant Human Relaxin Administration in *Macaca Facicularis*," Biology of Reproduction 71:1591-1597 (2004).

Lee, et al., "Interleukin-6. but not Relaxin, Predicts Outcome of Rescue Cerclage in Women with Cervical Incompetence," *American Journal of Obstetrics and Gynecology* 191:784-789 (2004).

Petersen, et al., "Variations in Serum Relaxin (hRLX-2) Concentrations During Human Pregnancy," *Acta Obstet Gynecol Scand* 74:251-256 (1995).

Ryan, et al., "Systemic Relaxin in Pregnant Pony Mares Grazed in Endophyte-infected Fescue: Effects of Fluphenazine Treatment," *Theriogenology* 56:471-483 (2001).

Stewert, et al., "The Relationship Between hCG and Relaxin Secretion in Spontaneous Abortions," Clinical *Endocrinology* 38:379-385 (1993).

\* cited by examiner

METHODS AND COMPOSITIONS FOR CONTROL OF FETAL GROWTH VIA MODULATION OF RELAXIN

CROSS-REFERENCE TO RELATED APPLICATIONS

This application claims the benefit of U.S. provisional patent application No. 60/567,353, filed Apr. 30, 2004, the disclosure of which is incorporated herein by reference in its entirety for all purposes.

BACKGROUND OF THE INVENTION

Intrauterine growth retardation ("IUGR") is a syndrome whereby the size or growth rate of a fetus is unusually small for the gestational age of the fetus. Fetuses weighing below the 10th percentile for their gestational age, are by definition afflicted with IUGR. IUGR can result from a wide variety of causes, all of which result in the failure of a fetus to exhibit a normal rate of growth. Small for gestational age (SGA) babies are defined as birth weight and/or length at least 2 standard deviations below the mean for gestational age (Lee et al., 2003, Pediatrics 111: 1253-1261). Although some fetuses that are small for their gestational age can be simply constitutionally small and not otherwise unhealthy, other causes, such as placental insufficiency, infection, and genetic disorders, can result in significant perinatal morbidity and mortality. The individuals so affected are also more likely to suffer from abnormal structure, function, and disease in later life. Any method to reverse or ameliorate IUGR can thus provide significant benefits to these offspring.

A number conditions have been identified as increasing the risk that a fetus will display IUGR. Often, the primary effect of these conditions is to cause placental insufficiency (Lepercq and Mahieu-Caputo, 1998, Horm. Res. 49(suppl 2): 14-19). These conditions include maternal weight and height prior to pregnancy and low weight gain during the pregnancy; maternal history of stillbirth, neonatal death, and previous offspring with low birth weight; maternal activities during pregnancy, such as smoking, alcohol and drug use, and poor nutrition; early intrauterine infections; maternal medical diseases; multiparous pregnancies; and various complications arising during pregnancy.

The maternal endocrine system likely has a role in controlling fetal growth rates, e.g., by regulating the placental nutrient supply. Insulin and insulin-like growth factor I have been shown to be involved in this process (Gluckman et al., 1990, Acta Paediatr. Scand. [Suppl] 367:105-110; U.S. Pat. No. 5,420,111).

Recent studies have suggested that VEGF activity is critical to normal placental development (reviewed in Tsatsaris et al., 2003, J Clin Endocrinol Metab 88:5555-5563). The imbalance between expression of members of the VEGF family (including VEGF-A and placental growth factor (PlGF)) and their soluble and cell-associated receptors (s-flt and flt, respectively) may play a role in conditions associated with placental insufficiency. It is currently believed that upregulation of s-flt, which can antagonize VEGF and PlGF activity, shifts the balance of this family toward anti-angiogenic activity, thus interfering with normal vascular development of the placenta. It is also believed that inadequate placental perfusion may be upstream of maternal disorders, such as preeclampsia (Bdolah et al., 2004, Semin Nephrol 24:548-556), HELLP (Cho et al., 2003, J Korean Med Sci 18:402-428), as well as abnormal or inadequate fetal growth (Ahmed and Perkins, 2000, Baillieres Best Pract Res Clin Obstet Gynecol 14:981-998). Treatments that can prolong pregnancy are likely to be beneficial in allowing both short-term fetal growth and obviation of long term developmental impairment.

Because of the current lack of effective treatments for IUGR or placental insufficiency, there is a strong need to develop new therapeutic approaches for this condition.

BRIEF SUMMARY OF THE INVENTION

The present invention provides compositions and methods for the treatment, diagnosis and prevention of conditions, disorders or diseases involving fetal growth, including, but not limited to, intrauterine growth retardation ("IUGR") and placental insufficiency. The invention provides methods for modulating signaling pathways related to the polypeptide hormone, relaxin. More particularly, the present invention provides methods relating to the modulation of relaxin synthesis, relaxin receptor synthesis, relaxin binding to its receptor, and relaxin signaling.

The present invention also provides methods for the identification and prophylactic or therapeutic use of compounds in the treatment and diagnosis of conditions, disorders, or diseases involving fetal growth, including, but not limited to, intrauterine growth retardation ("IUGR") and placental insufficiency. Additionally, methods are provided for the diagnostic monitoring of patients undergoing clinical evaluation for the treatment of conditions or disorders involving fetal growth, for monitoring the efficacy of compounds in clinical trials and for identifying subjects who may be predisposed to such conditions, disorders, or diseases involving fetal growth.

Specifically, in one embodiment the invention provides a method of increasing intrauterine fetal growth rate, comprising the step of administering to a pregnant mammal a therapeutically effective amount of relaxin for a time sufficient to increase fetal growth rate. In related embodiments, the relaxin is administered during the first, second, and/or third trimester of pregnancy. In another related embodiment, the relaxin is administered for at least 2 weeks starting at ovulation. In yet another embodiment, the relaxin is administered before and after ovulation. In yet another embodiment, the relaxin is administered for about a week before ovulation and about four weeks after ovulation.

In another embodiment, the invention provides a method of increasing intrauterine fetal growth rate wherein the relaxin is administered in an amount sufficient to result in the birth of a baby of at least around normal birth weight. In a related embodiment, the relaxin is administered in an amount sufficient to maintain a serum concentration in the pregnant mammal of at least around 1 ng/mL. In yet another related embodiment, the relaxin may be administered parenterally or by continuous subcutaneous infusion or intravaginally. In yet another embodiment, the relaxin is administered at a dose between 10 μg/kg/day-and 200 μg/kg/day.

In another embodiment, the invention provides a method of increasing intrauterine fetal growth rate comprising the step of administering to a pregnant mammal a therapeutically effective amount of relaxin for a time sufficient to increase fetal growth rate, wherein the increase in fetal growth rate is assessed by an imaging technique. In a related embodiment, the imaging technique is selected from the group consisting of ultrasonic imaging and magnetic resonance imaging. In yet another embodiment, the pregnant mammal is diagnosed as hosting a fetus with intrauterine growth retardation. In one embodiment, the diagnosis of intrauterine growth retardation is obtained through the use of an imaging technique, e.g., ultrasonic imaging or magnetic resonance imaging.

In another embodiment, the invention provides a method of increasing intrauterine fetal growth rate comprising the step of administering to a pregnant mammal a therapeutically effective amount of relaxin wherein the mammal has a condition that increases the risk of fetal intrauterine growth retardation or low birth weight. In a related embodiment, the condition that increases the risk of fetal intrauterine growth retardation is selected from the group consisting of lupus, hyperthyroidism, hypertension, preeclampsia, malarial infection, serum antiphospholipid antibodies, a history of recurrent spontaneous abortion, a history of intrauterine growth retardation, a history of having children with low birth weight, a multiple-gestation pregnancy, and a pregnancy resulting from in vitro fertilization and embryo transfer.

In some embodiments, the methods of the invention may be use to treat pregnant humans. In other embodiments, the methods may be used to treat other pregnant mammals, e.g., a horse, cow, sheep, pig, deer, dog, cat, rat, or a mouse.

The invention also provides, in one embodiment, a method of reducing the risk or incidence of spontaneous abortion in a pregnant mammal, the method comprising administering to the pregnant mammal an amount of relaxin effective to reduce the risk or incidence of spontaneous abortion. the relaxin is administered during the first trimester of pregnancy. In related embodiments, the relaxin is administered during the first, second, and/or third trimester of pregnancy. In another related embodiment, the relaxin is administered for at least 2 weeks starting at ovulation. In yet another embodiment, the relaxin is administered before and after ovulation. In yet another embodiment, the relaxin is administered for about a week before ovulation and about four weeks after ovulation. In yet another embodiment, the relaxin is administered in an amount sufficient to maintain a serum concentration of at least about 1 ng/ml.

In another embodiment, the invention provides a method for determining whether a subject has an increased risk for developing a condition associated with placental insufficiency, comprising the steps of measuring the level of relaxin expression in said subject, comparing said measured level of relaxin to a level of relaxin associated with normal placental development in an appropriate control subject, wherein a lower measured level of relaxin correlates with an increased risk of developing said condition. In a related embodiment, the subject is pregnant. In a related embodiment, the placental insufficiency is selected from the group consisting of IUGR, SGR, and preeclampsia. In yet other related embodiments, the relaxin expression is measured in serum or tissue. In yet another embodiment, the level of level of relaxin expression is measured by determining the level of transcription of a gene encoding relaxin. In yet another related embodiment, the subject has previously been diagnosed with intrauterine growth retardation, placental insufficiency, or preeclampsia. In yet another related embodiment, the method further comprises treating said subject with a therapeutic amount of relaxin. In yet another embodiment, the relaxin is human H2 relaxin. In yet another embodiment, the relaxin is selected from the group consisting of H1, H2 or H3 relaxin. In yet another embodiment, the method comprises testing the subject to determine whether levels of HIF-1α or HGF have increased.

In yet another embodiment, the invention provides a method for determining whether a subject has an increased risk for developing a condition associated with placental insufficiency, comprising determining a nucleotide sequence of at least a portion of a gene encoding relaxin in the subject, wherein the identification of a nucleotide sequence associated with the decreased expression or activity of the relaxin peptide indicates that the subject has an increased risk for developing said condition. In a related embodiment, the subject is pregnant. In a related embodiment, the condition is selected from the group consisting of IUGR, SGR, and preeclampsia. In yet another related embodiment, the subject has previously been diagnosed with intrauterine growth retardation, placental insufficiency, or preeclampsia. In yet another related embodiment, the method further comprises treating said subject with a therapeutic amount of relaxin. In yet another embodiment, the relaxin is human H2 relaxin. In yet another embodiment, the relaxin is selected from the group consisting of H1, H2 or H3 relaxin. In yet another embodiment, the method comprises testing the subject to determine whether levels of HIF-1α or HGF have increased.

In another embodiment, the invention provides a method for determining whether a subject has an increased risk for developing a condition associated with placental insufficiency, comprising determining a nucleotide sequence of at least a portion of a gene encoding an enzyme involved in the post-translational processing of relaxin, wherein the identification of a nucleotide sequence associated with the decreased activity of relaxin indicates that the subject has an increased risk for developing said condition. In a related embodiment, the condition is selected from the group consisting of IUGR, SGR, and preeclampsia. In a related embodiment, the subject is pregnant. In yet another related embodiment, the subject has previously been diagnosed with intrauterine growth retardation, placental insufficiency, or preeclampsia. In yet another related embodiment, the method further comprises treating said subject with a therapeutic amount of relaxin. In yet another embodiment, the relaxin is human H2 relaxin. In yet another embodiment, the relaxin is selected from the group consisting of H1, H2 or H3 relaxin. In yet another embodiment, the method comprises testing the subject to determine whether levels of HIF-1α or HGF have increased.

In another embodiment, the invention provides a method for treating placental insufficiency in a subject, comprising: diagnosing placental insufficiency in the subject, and administering a therapeutically effective amount of relaxin to treat the placental insufficiency. In yet another related embodiment, the subject has previously been diagnosed with intrauterine growth retardation, placental insufficiency, or preeclampsia. In yet another related embodiment, the method further comprises treating said subject with a therapeutic amount of relaxin. In yet another embodiment, the relaxin is human H2 relaxin. In yet another embodiment, the relaxin is selected from the group consisting of H1, H2 or H3 relaxin. In yet another embodiment, the method comprises testing the subject to determine whether levels of HIF-1α or HGF have increased.

DETAILED DESCRIPTION OF THE INVENTION

Figure 1:
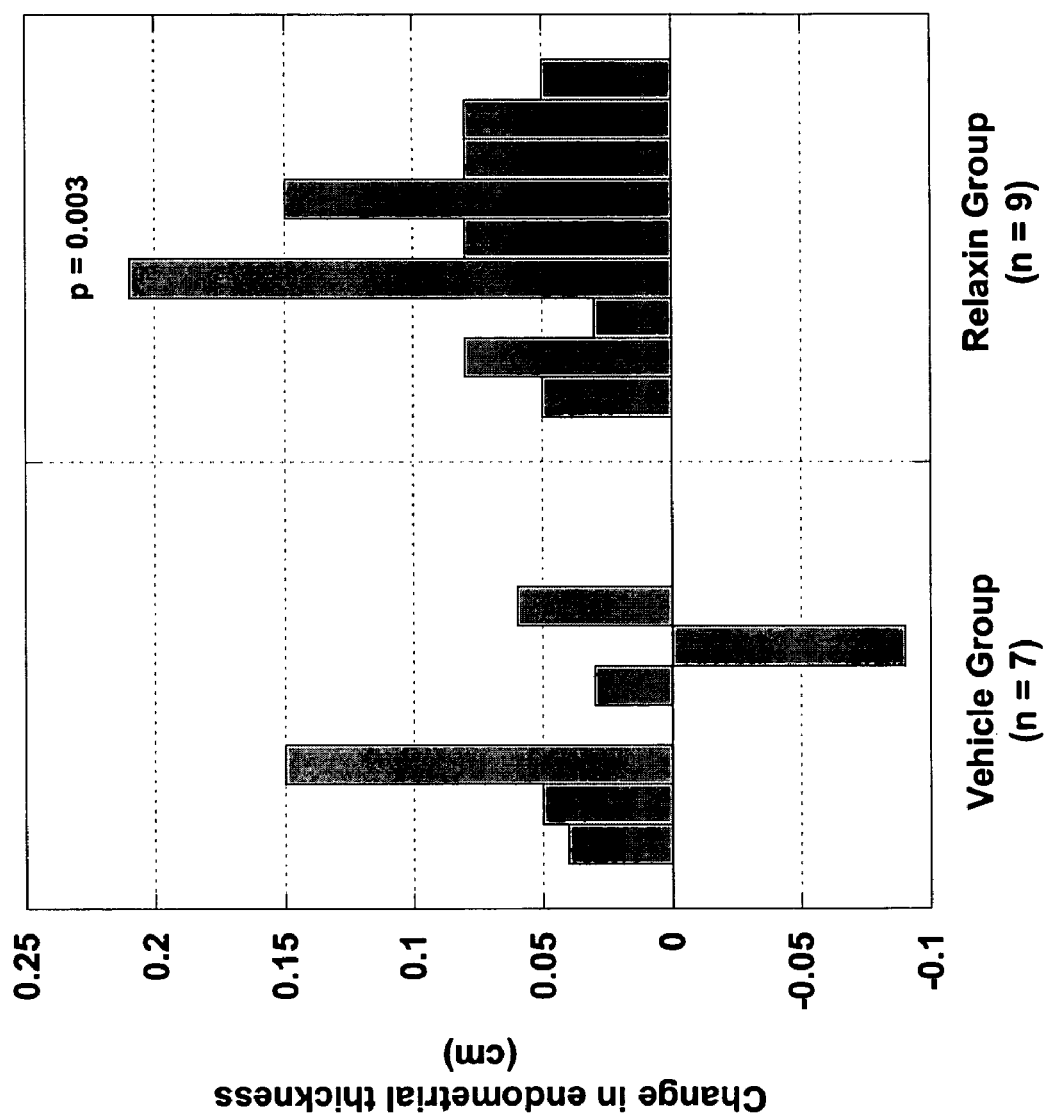
FIG. 1 shows the change in endometrial thickness between Day 0-Day 7 in vehicle- and relaxin-treated female cynomolgus monkeys. Two endometrial thickness measurements were made in each of the sagittal and transverse planes for each female, and were averaged to yield one thickness measurement for each female on each of Days 0 and 7. Thickness increased in all females in the relaxin group (p=0.003, paired t-test), whereas it increased in five of the seven females in the vehicle-treated group (NS).

Definitions:

The following terms used herein shall have the meaning indicated:

Relaxin receptor antagonist, as used herein, refers to a factor which neutralizes or impedes or otherwise reduces the action or effect of a relaxin receptor. Such antagonists can include compounds that bind relaxin or that bind the relaxin receptor. Such antagonists can also include compounds that neutralize, impede or otherwise reduce relaxin receptor output, that is, intracellular steps in the relaxin signaling pathway following binding of relaxin to the relaxin receptor, i.e., downstream events that affect relaxin/relaxin receptor signaling, that do not occur at the receptor/ligand interaction level. Relaxin receptor agonists may include, but are not limited to proteins, oligonucleotides, carbohydrates, and small organic molecules.

Relaxin receptor agonist, as used herein, refers to a factor which activates, induces or otherwise increases the action or effect of a relaxin receptor. Such agonists can include compounds that bind relaxin or that bind the relaxin receptor. Such antagonists can also include compounds that activate, induce or otherwise increase relaxin receptor output, that is, intracellular steps in the relaxin signaling pathway following binding of relaxin to the relaxin receptor, i.e., downstream events that affect relaxin/relaxin receptor signaling, that do not occur at the receptor/ligand interaction level. Relaxin receptor agonists may include, but are not limited to proteins, oligonucleotides, carbohydrates, and small organic molecules.

A therapeutically effective amount is the amount of an agent that upon administration to a recipient mammal results in a desired change in the physiology of the mammal, e.g., results in an increase or decrease in fetal or placental growth relative to that of a corresponding control mammal not administered the agent.

A pregnant mammal is, for purposes of the invention, a mammal carrying one or more developing offspring within its body. The pregnant mammal may have conceived naturally or may have become pregnant through an artificial technique such as in vitro fertilization and embryo transfer. The developing offspring may be either at the embryonic or fetal stage, depending on how much time has passed since fertilization. In humans, this transition occurs at about eight weeks following implantation of the embryo.

Mammal is defined for purposes of the invention as any of the various warm-blooded vertebrate animals of the class Mammalia.

Gestation, as used herein, refers to the period of development in the uterus from the time of conception until birth, and gestational age refers to the length of this time period.

Conception refers to the formation of one or more viable zygotes through the union of sperm and egg.

Birth refers to the emergence and separation of offspring from the mother, whether by natural or assisted means.

Although some risk factors for fetal growth abnormalities are known, and in some cases fetuses that suffer from growth abnormalities can be diagnosed, the current methods for screening, prognosis, and diagnosis of these conditions are less than ideal. In addition, there is currently no effective intrauterine therapy to treat the conditions. Instead, the status of the fetus is followed carefully in utero by ultrasonic diagnostic techniques, and the fetus is delivered as soon as it is likely to survive. For fetuses that have been diagnosed with a fetal growth abnormality, such as, for example, IUGR, at an early stage of gestation, determining the proper balance between the risks of leaving the fetus in utero and those of inducing the birth prematurely is extremely difficult. Because of the current lack of effective methods to screen, prognose, diagnose, and treat fetal growth abnormalities, there is a strong need to develop new approaches for these purposes.

One of the bases for the invention described herein is the unexpected discovery that relaxin modulates placental size and fetal growth in pregnant mammals. By way of actual working examples, results from preclinical studies using primate models are described in the Examples section. Treatment of the primates with relaxin caused an increase in the mean endometrial thickness of the animals, an increase in embryonic implantation rate, an apparent increase in placental surface area and size and, notably, an increase in the mean birth weight of the offspring. Without intending to be limited to a particular mechanism, it is believed that relaxin may have proangiogenic and differentiating effects on the endometrial lining of the uterus in primates, and that these effects may in turn affect placental sufficiency and birth weight. Administration of relaxin to human subjects has been associated with heavier than usual or prolonged menstrual bleeding (Unemori et al., 1999, *Hum. Reprod.* 14:800-6). Consistent with the in vivo findings, radiolabeled relaxin binds specifically and with high affinity to endometrial stromal cells in vitro. Furthermore, relaxin stimulates the expression of a specific angiogenic factor, vascular endothelial growth factor ("VEGF"), in these cells.

Relaxin Protein Polypeptides and Nucleic Acids

Relaxin proteins and nucleic acids (sense and antisense) can be utilized as part of the therapeutic, diagnostic, prognostic and screening methods of the present invention. For example, relaxin proteins, polypeptides and peptide fragments, mutated, truncated or deleted forms of relaxin, and relaxin fusion proteins and other derivatives can be utilized.

As used herein, the term "relaxin" refers to a functional relaxin protein that is capable of effectively modulating fetal growth. The primary structure of the relaxin protein can correspond to a native relaxin sequence or to sequences differing from the native relaxin sequence by up to about three conservative amino acid substitutions. Alternatively, the structure can correspond to sequences containing an A chain that may be truncated by up to about six amino acids from the N-terminus and/or up to about six amino acids from the C-terminus and containing a B chain that may be truncated by up to about six amino acids from the N-terminus and/or up to about six amino acids from the C-terminus. Functional relaxin proteins containing small insertions and/or extensions also fall within the scope of the invention as do relaxin molecules that have been chemically modified. Examples of chemical modifications that can be used in the invention include, but are not limited to, substitution of a D-amino acid for an L-amino acid, glycosylation of an amino acid side chain, alkylation of an amino acid side chain or N-terminus, acylation of an amino acid side chain or N-terminus, esterification of an amino acid side chain or C-terminus, phosphorylation of an amino acid side chain, sulfation of an amino acid side chain, and hydroxylation of an amino acid side chain. Examples of functional relaxin analogues and modified relaxins have been reported. (See U.S. Pat. No. 5,023,321; U.S. Pat. No. 5,811, 395.) For simplicity, relaxins that differ from a native relaxin either by changes in the sequence or by chemical modification will be referred to as "relaxin variants".

For purposes of the invention, a relaxin is considered functional if its activity is not significantly diminished from the activity of a native relaxin. Activity of relaxins can be assessed functionally by comparison of the effects of the relaxin variant and native relaxin on fetal growth in pregnant mammals. A relaxin variant having more than 10% of the effects of the native relaxin is considered functional. Whether or not a relaxin variant retains activity can alternatively be determined using assays known in the art for detecting relaxin activity. For example, bioassays used for the measurement of active relaxin during pregnancy and non-pregnancy, are described in the literature (Steinetz et al., 1960, *Endocrinology* 67:102-115; Sarosi et al., 1983, *Am. J. Obstet. Gynecol.* 145:402-5; Erikson and Liu, 2001, Proceedings from the Relaxin Congress). Effects of relaxin and relaxin variants on the stimulation of VEGF expression in cultured endometrial cells is another basis for determining the activity of the variants (Unemori et al., 1999, *Hum. Reprod.* 14:800-806). Relaxin variants having more than 10% of the activity of a native relaxin in these assays are considered functional.

The native relaxins used in the invention can correspond to relaxin from any species, including, but not limited to, horse, cow, sheep, pig, deer, dog, cat, rat, mouse, and preferably human. For use in modulating fetal growth in humans, the relaxin will preferably be recombinant human relaxin H2 ("rhRLX"). The cloning of the genes encoding this polypeptide and two other forms of relaxin have been reported (Hudson et al., 1983, *Nature* 301:628-631; Hudson et al., 1984, Bathgate et al., 2002, J Biol Chem 277:1148-1157; *EMBO J.* 3:2333-2339; U.S. Pat. No. 4,758,516; U.S. Pat. No. 4,871, 670). The predicted sequences of the relaxins encoded by the three genes are substantially different. Only the H2 form of the relaxin peptide has been detected to date in the blood and tissues, including the ovaries. Other analogues and derivatives of relaxin have recently been synthesized and found to have significant biological activity (see, for example, U.S. Pat. No. 5,811,395).

The cellular receptor for relaxin has also been cloned (Hsu et al., *Science* 295:671-674, 2002), and the presence of relaxin receptors (LGR7) in various tissues and in cultured cell lines has been established through detection of LGR7 transcripts (Shirota et al., 2004, *J Clin Endocrinol Metab* 90:516-521 Ivell, 2003; *Reprod Biol Endocrinol* 1:114; 2003; Luna et al., 2004 *Mol Hum Reprod* 10:85-90; Ivell et al., 2003, *Reprod Biol Endocrinol* 1:114), as well as with binding studies with radiolabeled relaxin probes (Osheroff et al., 1990, *J. Biol. Chem.* 265:9396-9401; Osheroff and King, 1995, *Endocrinol.*, 136:4377-4381; Parsell et al, 1996, *J. Biol. Chem.*, 271:27936-27941). Although elucidation of the molecular mechanisms underlying rhRLX bioactivity is not complete, signaling through the relaxin receptor is known to involve activation of MAPK, or ERK1/2 (Zhang et al., 2003, *J Cell Biochem*, 85:536-544; Dschietzig et al., 2003, *Circ Res.*, 92:32-40). as well as PI3K, PKA and tyrosine phosphorylation (Bartsch et al., 2001, *Mol Hum Reprod.*, 7:799-809; Palejwala et al., 1998 *Endocrinology*, 139:1208-1247) pathways.

Because of its structural similarities to insulin, relaxin has been assigned to the insulin-related family of hormones (Blundell and Humbel, 1980, *Nature*, 287:781-787; Schwabe and Büllesbach, 1990, *Comp. Biochem. Physiol*, 96:15-21; Schwabe and Büllesbach, 1994, *FASEB J.* 8:1152-1160). Another member of this family was initially isolated from Leydig cells and, because its C-peptide is more similar in length to insulin than to relaxin, was initially termed Leydig insulin-like peptide (Adham et al., 1993, *J. Biol. Chem.*, 268: 26668-26672). This peptide has recently been renamed insulin-like peptide-3 (ISNL3), which binds to a receptor homologous to LGR7, called LGR8 (Kumagai et al., 2002, *J Biol Chem*, 277:31283-31286).

The relaxins can either be purified from a natural source, expressed in and purified from a recombinant DNA expression system, synthesized chemically, or produced by a combination of these methods. For example, the polypeptides corresponding to the A- and B-chains of the native relaxin or relaxin variant can be generated by chemical synthesis and/or by expression in recombinant DNA systems (U.S. Pat. No. 5,023,321; U.S. Pat. No. 5,320,953; U.S. Pat. No. 5,326,694). The desired disulfide bonding can be obtained by combining the reduced forms of the A- and B-chains in aqueous medium under appropriate conditions (U.S. Pat. No. 4,835,251; U.S. Pat. No. 5,464,756). Chemical modifications of the polypeptides can be performed at any time during the synthesis as desired. Appropriate formulation of native relaxins and variants for therapeutic use has been described (U.S. Pat. No. 5,451,572; U.S. Pat. No. 5,945,402).

The relaxins may advantageously be produced by recombinant DNA technology using techniques well known in the art for expressing nucleotide sequences. For purposes of the invention, the term "relaxin nucleotide sequences" refers not only to sequences encoding open reading frames, but also to upstream and downstream sequences within the relaxin gene. Similar methods also can be used to construct expression vectors containing relaxin nucleotide sequences. These methods include, for example, in vitro recombinant DNA techniques, synthetic techniques, and in vivo genetic recombination. See, Sambrook et al., 1989, *Molecular Cloning, A Laboratory Manual, Second Edition*, Cold Spring Harbor Press, N.Y., and Ausabel et al., 1989, *Current Protocols in Molecular Biology*, Green Publishing Associates and Wiley Interscience, N.Y., each of which is incorporated herein by reference in its entirety. Alternatively, RNA capable of encoding relaxin nucleotide sequences may be chemically synthesized using, for example, synthesizers. See, for example, the techniques described in *Oligonucleotide Synthesis*, 1984, Gait, M. J. ed., IRL Press, Oxford, which is incorporated by reference herein in its entirety.

A variety of host-expression vector systems may be utilized to express the relaxin nucleotide sequences of the invention. Where the relaxin peptide or polypeptide is a soluble derivative, the peptide or polypeptide can be recovered from the culture, i.e., from the host cell in cases where the relaxin peptide or polypeptide is not secreted, and from the culture media in cases where the relaxin peptide or polypeptide is secreted by the cells. However, the expression systems also encompass engineered host cells that express relaxin or functional equivalents in situ, i.e., anchored in the cell membrane. Purification or enrichment of relaxin from such expression systems can be accomplished using appropriate detergents and lipid micelles and methods well known to those skilled in the art. However, such engineered host cells themselves may be used in situations where it is important not only to retain the structural and functional characteristics of relaxin, but to assess biological activity, e.g., in drug screening assays.

The expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing relaxin nucleotide sequences; yeast (e.g., *Saccharomyces, Pichia*) transformed with recombinant yeast expression vectors containing the nucleotide sequences; insect cell systems infected with recombinant virus expression vectors (e.g., baculovirus) containing the sequences; plant cell systems infected with recombinant virus expression vectors (e.g., cauliflower mosaic virus, CaWV; tobacco mosaic virus, TMV) or transformed with recombinant plasmid expression vectors (e.g., Ti plasmid) containing the nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the relaxin gene product being expressed. For example, when a large quantity of such a protein is to be produced, for the generation of pharmaceutical compositions of relaxin protein or for raising antibodies to relaxin protein, for example, vectors which direct the expression of high levels of fusion protein products that are readily purified may be desirable. Such vectors include, but are not limited to, the *E. coli* expression vector pUR278 (Ruther et al., 1983, *EMBO J.* 2:1791), in which the relaxin coding sequence may be ligated into the vector in frame with the lacZ coding region so that a fusion protein is produced; pIN vectors (Inouye and Inouye, 1985, *Nucleic Acids Res.* 13:3101-3109; Van Heeke and Schuster, 1989, *J. Biol. Chem.* 264:5503-5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. The relaxin gene coding sequence may be cloned into non-essential regions (for example the polyhedrin gene) of the virus and placed under control of an AcNPV promoter (for example the polyhedrin promoter). Successful insertion of a relaxin nucleotide sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, *J. Virol.* 46:584; Smith, U.S. Pat. No. 4,215,051).

In mammalian host cells, a number of viral-based expression systems may be utilized. In cases where an adenovirus is used as an expression vector, the relaxin nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the relaxin gene product in infected hosts (e.g., Logan and Shenk, 1984, *Proc. Natl. Acad. Sci. USA* 81:3655-3659). Specific initiation signals may also be required for efficient translation of inserted relaxin nucleotide sequences. These signals include the ATG initiation codon and adjacent sequences. In cases where an entire relaxin gene or cDNA, including its own initiation codons and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (e.g., Bittner et al., 1987, *Meth. Enzymol.* 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and W138 cell lines.

For long-term, high-yield production of recombinant proteins, stable expression is preferred. For example, cell lines which stably express a relaxin nucleotide sequence may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express relaxin gene products. Such engineered cell lines may be particularly useful in screening and evaluation of compounds that affect the endogenous activity of relaxin.

A number of selection systems may be used, including but not limited to, the herpes simplex virus thymidine kinase (Wigler, et al., 1977, *Cell* 11:223), hypoxanthine-guanine phosphoribosyltransferase (Szybalska and Szybalski, 1962, *Proc. Natl. Acad. Sci. USA* 48:2026), and adenine phosphoribosyltransferase (Lowy, et al., 1980, *Cell* 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, *Proc. Natl. Acad. Sci. USA* 77:3567; O'Hare, et al., 1981, *Proc. Natl. Acad. Sci. USA* 78:1527); gpt, which confers resistance to mycophenolic acid (Mulligan and Berg, 1981, *Proc. Natl. Acad. Sci. USA* 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147).

The relaxin gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate the transgenic animals.

Any technique known in the art may be used to introduce the relaxin transgene into animals or to "knock-out" or inactivate endogenous relaxin to produce the founder lines of transgenic animals. Such animals can be utilized as part of the screening methods of the invention, and cells and/or tissues from such animals can be obtained for generation of additional compositions (e.g., cell lines, tissue culture systems) that can also be utilized as part of the screening methods of the invention.

Techniques for generation of such animals are well known to those of skill in the art and include, but are not limited to, pronuclear microinjection (Hoppe, P. C. and Wagner, T. E., 1989, U.S. Pat. No. 4,873,191); retrovirus mediated gene transfer into germ lines (Van der Putten et al., 1985, *Proc. Natl. Acad. Sci. USA* 82:6148-6152); gene targeting in embryonic stem cells (Thompson et al., 1989, *Cell* 56:313-321); electroporation of embryos (Lo, 1983, *Mol. Cell. Biol.* 3:1803-1814); and sperm-mediated gene transfer (Lavitrano et al., 1989, *Cell* 57:717-723); etc. For a review of such techniques, see Gordon, 1989, Transgenic Animals, *Intl. Rev. Cytol.* 115:171-229, which is incorporated by reference herein in its entirety.

With respect to transgenic animals containing a transgenic relaxin, such animals can carry a relaxin transgene in all their cells. Alternatively, such animals can carry the transgene or transgenes in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, *Proc. Natl. Acad. Sci. USA* 89:6232-6236). The regulatory sequences required for such a cell-type specific activation will depend upon the particular cell type of interest, and will be apparent to those of skill in the art. When it is desired that the transgene be integrated into the chromosomal site of the endogenous gene, gene targeting is preferred. Briefly, when such a technique is to be utilized, vectors containing some nucleotide sequences homologous to the endogenous relaxin gene are designed for the purpose of integrating, via homologous recombination with chromosomal sequences, into and disrupting the function of the nucleotide sequence of the endogenous relaxin gene. The transgene may also be selectively introduced into a particular cell type, thus inactivating the endogenous relaxin gene in only that cell type, by following, for example, the teaching of Gu, et al., 1994, *Science* 265:103-106. The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of tissue that expresses the relaxin gene, may also be evaluated immunocytochemically using antibodies specific for the transgene product.

Antibodies to Relaxin

Antibodies that specifically recognize and bind to one or more epitopes of relaxin, or epitopes of conserved variants of relaxin, or peptide fragments of relaxin can be utilized as part of the methods of the present invention. Such antibodies include, but are not limited to, polyclonal antibodies, monoclonal antibodies (mAbs), human, humanized or chimeric antibodies, single chain antibodies, Fab fragments, F(ab')$_2$ fragments, fragments produced by a Fab expression library, anti-idiotypic (anti-Id) antibodies and epitope-binding fragments of any of the above.

Such antibodies may be used, for example, as part of the diagnostic or prognostic methods of the invention for diagnosing fetal growth abnormalities in a pregnant mammal by measuring relaxin levels in the mammal, e.g., relaxin levels in the blood serum of the mammal. Such antibodies may also be utilized in conjunction with, for example, compound screening schemes, as described below, for the evaluation of the effect of test compounds on expression and/or activity of the relaxin gene product. Additionally, such antibodies can be used in therapeutic and preventative methods of the invention. For example, such antibodies can correspond to relaxin receptor agonists or antagonists. Further, such antibodies can be administered to lower relaxin levels in the serum, for example by increasing the rate at which relaxin is removed from circulation.

For the production of antibodies, various host animals may be immunized by injection with relaxin, a truncated relaxin, functional equivalents of relaxin, or mutants of relaxin. Such host animals may include, but are not limited to, rabbits, mice, and rats, to name but a few. Various adjuvants may be used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein (Kohler and Milstein, 1975, *Nature* 256:495-497; and U.S. Pat. No. 4,376,110), the human B-cell hybridoma technique (Kosbor et al., 1983, *Immunology Today* 4:72; Cole et al., 1983, *Proc. Natl. Acad. Sci. USA* 80:2026-2030), and the EBV-hybridoma technique (Cole et al., 1985, *Monoclonal Antibodies And Cancer Therapy*, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

Additionally, recombinant antibodies, such as chimeric and humanized monoclonal antibodies, comprising both human and non-human portions, which can be made using standard recombinant. DNA techniques, are within the scope of the invention. A chimeric antibody is a molecule in which different portions are derived from different animal species, such as those having a variable region derived from a murine mAb and a human immunoglobulin constant region. See, e.g., Cabilly et al., U.S. Pat. No. 4,816,567; and Boss et al., U.S. Pat. No. 4,816,397, which are incorporated herein by reference in their entirety. Humanized antibodies are antibody molecules from non-human species having one or more complementarily determining regions (CDRs) from the non-human species and a framework region from a human immunoglobulin molecule. See, e.g., Queen, U.S. Pat. No. 5,585,089, which is incorporated herein by reference in its entirety. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, *Science* 240:1041-1043; Liu et al., 1987, *Proc. Natl. Acad. Sci. USA* 84:3439-3443; Liu et al., 1987, *J. Immunol.* 39:3521-3526; Sun et al., 1987, *Proc. Natl. Acad. Sci. USA* 84:214-218; Nishimura et al., 1987, *Canc. Res.* 47:999-1005; Wood et al., 1985, *Nature* 314:446-449; and Shaw et al., 1988, *J. Natl. Cancer Inst.* 80:1553-1559); Morrison, 1985, Science 229:1202-1207; Oi et al., 1986, *Bio/Techniques* 4:214; U.S. Pat. No. 5,225,539; Jones et al., 1986, *Nature* 321:552-525; Verhoeyan et al., 1988, *Science* 239:1534; and Beidler et al., 1988, *J. Immunol.* 141:4053-4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar, 1995, *Int. Rev. Immunol.* 13:65-93. For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1994, *Bio/technology* 12:899-903).

Alternatively, techniques described for the production of single chain antibodies (U.S. Pat. No. 4,946,778; Bird, 1988, *Science* 242:423-426; Huston et al., 1988, *Proc. Natl. Acad. Sci. USA*, 85:5879-5883; and Ward et al., 1989, *Nature* 334:544-546) can be adapted to produce single chain antibodies against relaxin gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, *Science,* 246:1275-1281) to allow rapid and easy identification of monoclonal Fab fragments with the desired specificity.

Antibodies to relaxin can, in turn, be utilized to generate anti-idiotype antibodies that "mimic" relaxin, using techniques well known to those skilled in the art. (See, e.g., Greenspan and Bona, 1993, *FASEB J* 7:437-444; and Nissinoff, 1991, *J. Immunol.* 147:2429-2438). For example, antibodies that bind to the portion of relaxin that interacts with the relaxin receptor could be used to generate anti-idiotype antibodies that mimic the receptor-binding region of relaxin and that may function as receptor agonists or antagonists. These antibodies could thus be useful for treatment of IUGR or other fetal growth abnormalities by modulation of fetal growth.

Diagnosis and Prognosis of Fetal Growth Abnormalities or Placental Insufficiency A variety of methods can be employed for the diagnostic and prognostic evaluation of abnormal fetal growth or placental insufficiency and for the identification of subjects having a predisposition to such diseases or states.

In particular, fetal growth abnormalities which can be diagnosed or prognosed in accordance with the present invention include conditions characterized by fetuses that are small for their gestational age, including, but not limited to intrauterine growth retardation.

Thus, in accordance with this aspect of the present invention, there is a method of diagnosing or prognosing a fetal growth abnormality in a pregnant mammal, such as a pregnant human, comprising:

(a) measuring relaxin levels in blood serum of a pregnant mammal, e.g., a pregnant mammal suspected of exhibiting or being at risk for the fetal growth abnormality; and (b) comparing the level measured in (a) to the relaxin level in control blood serum, so that if the level obtained in (a) is lower than that of the control, the mammal is diagnosed as exhibiting or being at risk for the fetal growth abnormality, wherein the fetal growth abnormality is characterized by fetuses that are small for their gestational age.

Further, fetal growth abnormalities which can be diagnosed or prognosed in accordance with the present invention include conditions characterized by fetuses that are large for their gestational age, including, but not limited to diabetes.

Thus, in accordance with this aspect of the present invention, there is a method of diagnosing or prognosing a fetal growth abnormality in a pregnant mammal, such as a pregnant human, comprising:

(a) measuring relaxin levels in blood serum of a pregnant mammal, e.g., a pregnant mammal suspected of exhibiting or being at risk for the fetal growth abnormality; and (b) comparing the level measured in (a) to the relaxin level in control blood serum, so that if the level obtained in (a) is higher than that of the control, the mammal is diagnosed as exhibiting or being at risk for the fetal growth abnormality, wherein the fetal growth abnormality is characterized by fetuses that are large for their gestational age.

Additionally, methods are provided for the diagnostic monitoring of patients undergoing clinical evaluation for the treatment of fetal growth abnormalities, and for monitoring the efficacy of compounds in clinical trials.

Thus, in yet another aspect of the present invention, there is a method of monitoring efficacy of a compound for treating a fetal growth abnormality in a pregnant mammal, such as a pregnant human, comprising:

(a) administering the compound to a pregnant mammal;

(b) measuring relaxin-levels in blood serum of the mammal; and (c) comparing the level measured in (b) to the relaxin level in blood serum of the mammal prior to administering the compound, thereby monitoring the efficacy of the compound, wherein the fetal growth abnormality is characterized by fetuses that are small for their gestational age. Preferred compounds are ones that increase relaxin levels relative to that observed prior to administration.

In accordance with yet another aspect of the present invention, there is a method of monitoring efficacy of a compound for treating a fetal growth abnormality in a pregnant mammal, such as a pregnant human, comprising:

(a) administering the compound to a pregnant mammal;

(b) measuring relaxin levels in blood serum of the mammal; and (c) comparing the level measured in (b) to the relaxin level in blood serum of the mammal prior to administering the compound, thereby monitoring the efficacy of the compound, wherein the fetal growth abnormality is characterized by fetuses that are large for their gestational age. Preferred compounds are ones that decrease relaxin levels relative to that observed prior to administration.

Methods such as these can also be utilized for monitoring of patients undergoing clinical evaluation for treatment of fetal growth abnormalities. Generally, such methods further include a monitoring of the size of the fetus with respect to its gestational age.

Methods described herein may, for example, utilize reagents such as the relaxin nucleotide sequences described above and known to those of skill in the art (e.g., U.S. Pat. No. 4,758,516; U.S. Pat. No. 4,871,670), and relaxin antibodies, as described, in Section 5.1.1. Such reagents may be used, for example, for: (1) the detection of the presence of relaxin gene mutations; (2) the detection of either over- or under-expression of relaxin mRNA relative to controls displaying normal fetal growth; (3) the detection of either an over- or an under-abundance of relaxin gene product relative to controls displaying normal fetal growth; and (4) the detection of perturbations or abnormalities in the signal transduction pathway mediated by relaxin.

The methods described herein may be performed in conjunction with, prior to, or subsequent to techniques for measuring fetal size and growth. For example, upon identifying a mammal (e.g., human) exhibiting higher or lower levels of relaxin (e.g., in the blood serum) relative to that of a corresponding control mammal, the size and growth rate of one or more fetuses carved by the mammal can be measured to further clarify whether the fetus(es) exhibit(s) abnormal growth. If no abnormal fetal growth is observed, the mammal can be considered to be at risk for developing the condition, while if abnormal fetal growth is observed, the mammal exhibits the condition.

The methods described herein may be used together with diagnostic techniques to identify cases of abnormal fetal growth. Diagnosis typically involves an accurate assessment of both the size and gestational age of the fetus. An early ultrasonographic examination can be used to determine the gestational age (Benson and Doubilet, 1991, *AJR Am. J. Roentgenol.* 157:1275-1277). Other imaging techniques, such as magnetic resonance imaging, can also be used to estimate gestational age and to monitor intrauterine growth of the fetus as well as growth of the placenta. In the absence of an accurate estimate of gestational age, serial measurements of fetal size can also be used to assess whether or not fetal size is appropriate. An analysis of the use of morphometric and Doppler ultrasonic measurements indicates that abdominal circumference and estimated fetal weight—based on measurements of head size, abdominal size and femur length—are the best predictors of fetuses likely to be large or small for their gestational age (Chang et al., 1992, *Obstet. Gynecol.* 80:1030-8).

The methods described herein may be used to identify conditions of placental insufficiency, including but not limited to preeclampsia.

The methods described herein may be performed, for example, by utilizing pre-packaged diagnostic kits comprising at least one specific relaxin nucleotide sequence or relaxin antibody reagent, which may be conveniently used, e.g., in clinical settings, to diagnose patients exhibiting fetal growth abnormalities.

For the detection of relaxin mutations, any nucleated cell can be used as a starting source for genomic nucleic acid. For the detection of relaxin gene expression or gene products, any cell type or tissue in which the relaxin gene is expressed, such as, for example, granulosa lutein cells, may be utilized.

Nucleic acid-based detection techniques are described below, in Section 5.2.1. Peptide detection techniques are described below, in Section 5.2.2.

Detection of Relaxin Gene and Transcripts

Mutations within the relaxin gene can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving relaxin gene structure, including point mutations, insertions, deletions and chromosomal rearrangements. Such assays may include, but are not limited to; Southern analyses, single stranded conformational polymorphism analyses (SSCP), and PCR analyses.

Such diagnostic methods for the detection of relaxin gene-specific mutations can involve for example, contacting and incubating nucleic acids including recombinant DNA' molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, under conditions favorable for the specific annealing of these reagents to their complementary sequences within the relaxin gene, respectively. Preferably, the lengths of these nucleic acid reagents are at least 15 to 30 nucleotides. After incubation, all non-annealed nucleic acids are removed from the nucleic acid: relaxin gene hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents are easily removed. Detection of the remaining, annealed, labeled relaxin nucleic acid reagents is accomplished using standard techniques well-known to those in the art. The relaxin gene sequences to which the nucleic acid reagents have annealed can be compared to the annealing pattern expected from a normal relaxin gene sequence in order to determine whether a relaxin gene mutation is present.

Alternative diagnostic methods for the detection of relaxin gene specific nucleic acid molecules, in patient samples or other appropriate cell sources, may involve their amplification, e.g., by PCR (the experimental embodiment set forth in Mullis, 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of the relaxin gene in order to determine whether a relaxin gene mutation exists.

Additionally, well-known genotyping techniques can be performed to identify individuals carrying relaxin gene mutations: Such techniques include, for example, the use of restriction fragment length polymorphisms (RFLPs), which involve sequence variations in one of the recognition sites for the specific restriction enzyme used.

Additionally, improved methods for analyzing DNA polymorphisms which can be utilized for the identification of relaxin gene mutations have been described which capitalize on the presence of variable numbers of short, tandemly repeated DNA sequences between the restriction enzyme sites. For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks. is estimated to be 30,000-60,000 bp. Markers which are so closely spaced exhibit a high frequency co-inheritance, and are extremely useful in the identification of genetic mutations, such as, for example, mutations within the relaxin gene, and the diagnosis of diseases and disorders related to relaxin mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the relaxin gene, amplifying the extracted DNA, and labeling the repeat sequences to form a genotypic map of the individual's DNA.

The level of relaxin gene expression can also be assayed by detecting and measuring relaxin gene transcripts. For example, RNA from a cell type or tissue known, or suspected to express the relaxin gene, such as granulosa lutein cells, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the relaxin gene. Such analyses may reveal both quantitative and qualitative aspects of the expression pattern of the relaxin gene, including activation or inactivation of relaxin gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from within the relaxin nucleotide sequence as is well known to those of skill in the art. The preferred lengths of such nucleic acid reagents are at least 9-30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such relaxin gene expression assays "in situ", i.e., directly upon tissue sections (fixed and/or frozen) of patient tissue obtained from biopsies or resections, such that no nucleic acid purification is necessary. Nucleic acid reagents which are well known to those of skill in the art may be used as probes and/or primers for such in situ procedures (e.g. Nuovo, G. J., 1992, *PCR In situ Hybridization: Protocols and Applications*, Raven Press, NY).

Alternatively, if a sufficient quantity of the appropriate cells can be obtained, standard Northern analysis can be performed to determine the level of mRNA expression of the relaxin gene.

Detection of Relaxin Gene Products

Antibodies directed against wild type or mutant relaxin gene products or conserved variants or peptide fragments thereof, which are discussed, above, in Section 5.1.1, may also be used as diagnostics and prognostics for fetal growth abnormalities, as described herein. Such diagnostic methods may be used to detect abnormalities in the level of relaxin gene expression, or abnormalities in the structure and/or temporal, tissue, cellular, or subcellular location of relaxin, and may be performed in vivo or in vitro, such as, for example, on biopsy tissue. Antibodies can be labeled, e.g., with a radio-opaque or other appropriate compound and injected into a subject in order to visualize relaxin expressed in the body using methods such as X-rays, CAT-scans, or MRI.

Additionally, any relaxin fusion protein or conjugated protein whose presence can be detected, can be administered. For example, relaxin fusion or conjugated proteins labeled with a radio-opaque or other appropriate compound can be administered and visualized in vivo, as discussed, above—for labeled antibodies. Further such fusion proteins can be utilized for in vitro diagnostic procedures.

Alternatively, immunoassays or fusion protein detection assays, as described above, can be utilized on biopsy and autopsy samples in vitro to permit assessment of the expression pattern of relaxin. Such assays are not confined to the use of antibodies that define any particular epitope of relaxin. The use of these labeled antibodies will yield useful information regarding translation and secretion of relaxin from cells, and can identify defects in processing.

The tissue or cell type to be analyzed will generally include those which are known, or suspected, to express the relaxin gene, such as, for example, the ovaries. The protein isolation methods employed herein may, for example, be such as those described in Harlow and Lane (Harlow and Lane, 1988, *Antibodies: A Laboratory Manual*, Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the relaxin gene.

For example, antibodies, or fragments of antibodies, such as those described, above, in Section 5.1.1, useful in the present invention may be used to quantitatively or qualitatively detect the presence of relaxin gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection.

The antibodies (or fragments thereof) or relaxin fusion or conjugated proteins useful in the present invention may, additionally, be employed histologically, as in immunofluorescence, immunoelectron microscopy or non-immuno assays, for in situ detection of relaxin gene products or conserved variants or peptide fragments thereof, or for relaxin binding (in the case of labeled relaxin fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the relaxin gene product, or conserved variants or peptide fragments, or relaxin binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for relaxin gene products or conserved variants or peptide fragments thereof will typically comprise incubating a sample, such as a biological fluid (e.g., blood serum), a tissue extract, freshly harvested cells, or lysates of cells which have been incubated in cell culture, in the presence of a detectably labeled antibody capable of identifying relaxin gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with a labeled relaxin antibody or fusion protein. The solid phase support may then be washed with the buffer a second time to remove unbound antibody or fusion protein. The amount of bound label on solid support may then be detected by conventional means.

By "solid phase support or carver" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carver can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carvers for binding antibody or antigen, or will be able to ascertain the same by use of routine experimentation.

The binding activity of a given lot of relaxin antibody or fusion protein may be determined according to well known methods. Those skilled in the art will be able to determine operative and optimal assay conditions for each determination by employing routine experimentation.

With respect to antibodies, one of the ways in which the relaxin antibody can be detectably labeled is by linking the same to an enzyme for use in an enzyme immunoassay (EIA) (Voller, *The Enzyme Linked Immunosorbent Assay* (ELISA), 1978, Diagnostic Horizons 2:1-7, Microbiological Associates Quarterly Publication, Walkersville, Md.); Voller et al., 1978, *J. Clin. Pathol.* 31:507-520; Butler, 1981, *Meth. Enrymol.* 73:482-523; Maggio, E. (ed.), 1980, *Enzyme Immunoassay*, CRC Press, Boca Raton, Fla., Ishikawa, E. et al., (eds.), 1981, *Enzyme Immunoassay*, Kgaku. Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alphaglycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect relaxin through the use of a radioimmunoassay (RIA) (e.g. Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, therromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Screening Assays for Compounds Useful in the Treatment, Diagnosis and Prevention of Fetal Growth Abnormalities The present invention also provides screening methods (e.g., assays) for the identification of compounds which modulate fetal growth. The invention further encompasses agonists and antagonists of relaxin and relaxin receptors, including small molecules, large molecules, and antibodies, as well as nucleotide sequences that can be used to inhibit relaxin gene expression (e.g., antisense and ribozyme molecules), and gene or regulatory sequence replacement constructs designed to enhance relaxin gene expression (e.g., expression constructs that place the relaxin gene under the control of a strong promoter system). Such compounds may be used to modulate fetal growth.

In particular, cellular and non-cellular assays are described that can be used to identify compounds that interact with relaxin and relaxin receptors, e.g., modulate the activity of relaxin and relaxin receptors and/or bind to the relaxin receptor. The cell based assays can be used to identify compounds or compositions that affect the signal-transduction activity of relaxin and relaxin receptors, whether they bind to the relaxin receptor or act on intracellular factors involved in the relaxin signal transduction pathway. Such cell-based assays of the invention utilize cells, cell lines, or engineered cells or cell lines that express relaxin or relaxin receptors. The cells can be further engineered to incorporate a reporter molecule linked to the signal transduced by the activated relaxin receptor to aid in the identification of compounds that modulate relaxin and relaxin receptor signaling activity.

The invention also encompasses the use of cell-based assays or cell-lysate assays (e.g., in vitro transcription or translation assays) to screen for compounds or compositions that modulate relaxin gene expression. To this end, constructs containing a reporter sequence linked to a regulatory element of the relaxin gene can be used in engineered cells, or in cell lysate extracts, to screen for compounds that modulate the expression of the reporter gene product at the level of transcription. For example, such assays could be used to identify compounds that modulate the expression or activity of transcription factors involved in relaxin gene expression, or to test the activity of triple helix polynucleotides. Alternatively, engineered cells or translation extracts can be used to screen for compounds (including antisense and ribozyme constructs) that modulate the translation of relaxin mRNA transcripts, and therefore, affect expression of the relaxin gene.

The following assays are designed to identify compounds that interact with (e.g., bind to) relaxin or the relaxin receptor, compounds that interact with (e.g., bind to) intracellular proteins that interact with relaxin or the relaxin receptor, compounds that interfere with the interaction of relaxin or the relaxin receptor with transmembrane or intracellular proteins involved in relaxin receptor-mediated signal transduction, and compounds which modulate the activity of relaxin gene expression or modulate the level of relaxin or the relaxin receptor. Assays may additionally be utilized which identify compounds which bind to relaxin gene regulatory sequences (e.g., promoter sequences) and which may modulate relaxin gene expression. See e.g., Platt, 1994, *J. Biol. Chem.* 269: 28558-28562. Upon identification, compounds can further be tested for an ability to modulate relaxin signalling in vitro or in vivo, and can still further be tested for an ability to modulate fetal growth and to treat a fetal growth abnormality characterized by a fetus that is small or large for its gestational age.

Thus, in accordance with this aspects of the present invention, there is a method for identifying a compound to be tested for an ability to modulate (increase or decrease) fetal growth in a pregnant mammal, comprising:

(a) contacting a test compound with relaxin; and
(b) determining whether the test compound binds relaxin, so that if the test compound binds relaxin, then a compound to be tested for an ability to modulate fetal growth is identified.

Alternatively, there is a method for identifying a compound that modulates (increases or decreases) fetal growth in a pregnant mammal, comprising:

(a) contacting test compounds with relaxin;
(b) identifying a test compound that binds relaxin; and
(c) administering the test compound in (b) to a pregnant non-human mammal, and determining whether the test compound modulates fetal growth in the mammal relative to fetal growth in an untreated control pregnant non-human mammal, so that if the test compound modulates fetal growth, then a compound that modulates fetal growth in a pregnant mammal is identified.

In accordance with this, and other aspects of the present invention, a control pregnant non-human mammal, as used herein, is intended to mean a corresponding pregnant mammal that has not been administered the test compound.

In accordance with yet another aspect of the present invention, there is a method for identifying a compound to be tested for an ability to modulate (increase or decrease) fetal growth in a pregnant mammal, comprising:

(a) contacting a test compound with a relaxin polypeptide and cells that express a functional relaxin receptor for a time sufficient to form relaxin/relaxin receptor complexes; and
(b) measuring relaxin/relaxin receptor complex level, so that if the level measured differs from that measured in the absence of the test compound, then a compound to be tested for an ability to modulate fetal growth is identified.

In accordance with this, and other aspects of the present invention, relaxin/relaxin receptor complex formation can be measured by, for example, washing the cells and determining the amount complex formation by various assays well known to those of skill in the art.

In accordance with another aspect of the present invention, there is a method for identifying a compound to be tested for an ability to increase fetal growth in a pregnant mammal, comprising:

(a) contacting a test compound with cells that express a functional relaxin receptor; and
(b) determining whether the test compound activates the relaxin receptor, wherein if the compound activates the relaxin receptor a compound to be tested for an ability to increase fetal growth in a pregnant mammal is identified.

In accordance with this, and other aspects of the present invention, a functional relaxin receptor is a relaxin receptor that is capable of signal transduction following ligand binding to the active site of the receptor. Activation of the relaxin receptor, as used herein, is any increase in the activity (i.e., signal transduction) of the relaxin receptor.

In accordance with another aspect of the present invention, there is a method for identifying a compound that increases fetal growth in a pregnant mammal, comprising:

(a) contacting a test compound with cells that express a functional relaxin receptor, and determining whether the test compound activates the relaxin receptor;

(b) administering a test compound identified in (a) as activating the relaxin receptor to a pregnant non-human animal, and determining whether the test compound increases fetal growth of the animal relative to that of a corresponding control pregnant non-human animal, so that if the test compound increases fetal growth, then a compound that increases fetal growth in a mammal is identified.

In accordance with another aspect of the present invention, there is a method for identifying a compound to be tested for an ability to decrease fetal growth in a pregnant mammal, comprising:

(a) contacting a relaxin polypeptide and a test compound with cells that express a functional relaxin receptor, and (b) determining whether the test compound lowers activation of the relaxin receptor relative to that observed in the absence of the test compound; wherein a test compound that lowers activation of the relaxin receptor is identified as a compound to be tested for an ability to decrease fetal growth in a pregnant mammal.

In accordance with yet another aspect of the present invention, there is a method for identifying a compound that decreases fetal growth in a pregnant mammal, comprising:

(a) contacting a relaxin polypeptide and a test compound with cells that express a functional relaxin receptor, and determining whether the test compound lowers activation of the relaxin receptor;

(b) administering a test compound identified in (a) as lowering activation of the relaxin receptor to a pregnant non-human animal, and determining whether the test compound decreases fetal growth of the animal relative to that of a corresponding control pregnant non-human animal, so that if the test compound decreases fetal growth, then a compound that decreases fetal growth in a pregnant mammal is identified.

In accordance with yet another aspect of the invention, there is a method in which activation of a relaxin receptor is determined by measuring levels of phosphorylation of a high-molecular mass protein. This protein, which may be the relaxin receptor or another protein involved in relaxin signaling, is phosphorylated in uterine fibroblast cells in the presence of relaxin (Palejwala et al., 1998, *Endocrinol.* 139:1208-1212).

The compounds that may be screened in accordance with the invention include, but are not limited to, peptides, antibodies and fragments thereof, and other organic compounds (e.g., peptidomimetics) that bind to relaxin and/or the relaxin receptor and either mimic the activity triggered by the natural ligand (i.e., agonists) or inhibit the activity triggered by the natural ligand (i.e., antagonists); as well as peptides, antibodies or fragments thereof, and other organic compounds that mimic the ligand binding domain of the relaxin receptor (or a portion thereof) and bind to and "neutralize" natural ligand.

Such compounds may include, but are not limited to, peptides such as, for example, soluble peptides, including but not limited to members of random peptide libraries (e.g. Lam et al., 1991, *Nature* 354:82-84; Houghten et al., 1991, *Nature* 354:84-86), and combinatorial chemistry-derived molecular library made of D- and/or L-configuration amino acids, phosphopeptides (including, but not limited to, members of random or partially degenerate, directed phosphopeptide libraries; e.g. Songyang et al., 1993, *Cell* 72:767-778), antibodies (including, but not limited to, polyclonal, monoclonal, human, humanized, anti-idiotypic, chimeric or single chain antibodies, and FAb, $F(ab')_2$ and FAb expression library fragments, and epitope-binding fragments thereof), and small organic or inorganic molecules.

Other compounds which can be screened in accordance with the invention include, but are not limited to, small organic molecules that are able to gain entry into an appropriate cell and affect the expression of the relaxin or relaxin receptor gene or some other gene involved in the relaxin receptor signal transduction pathway (e.g., by interacting with the regulatory region or transcription factors involved in gene expression); or such compounds that affect the activity of the relaxin receptor (e.g., by inhibiting or enhancing the activity of the signaling domain) or the activity of some other intracellular factor involved in the relaxin receptor signal transduction pathway.

Computer modeling and searching technologies permit identification of compounds, or the improvement of already identified compounds, that can modulate relaxin or relaxin receptor expression or activity. Having identified such a compound or composition, the active sites or regions are identified. Such active sites might typically be ligand binding sites, such as the interaction domains of relaxin with the relaxin receptor itself. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the stricture of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential relaxin or relaxin receptor modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner, systematic variations in composition, such as by varying side groups, can be quickly evaluated to obtain modified modulating compounds or ligands of improved specificity or activity.

Further experimental and computer modeling methods useful to identify modulating compounds based upon identification of the active sites of relaxin, the relaxin receptor, and related transduction and transcription factors will be apparent to those of skill in the art.

Examples of molecular modeling systems are the CHARMm and QUANTA programs (Polygon Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, *Acta Pharmaceutical Fennica* 97:159-166; Ripka, *New Scientist* 54-57 (Jun. 16, 1988); McKinaly and Rossmann, 1989, *Annu. Rev. Pharmacol. Toxiciol.*, 29:111-122; Perry and Davies, *OSAR: Quantitative Structure Activity Relationships in Drug Design*, pp. 189-193 (Alan R. Liss, Inc. 1989); Lewis and Dean, 1989 *Proc. R. Soc. Lond.* 236:125-140 and 141-162; and, with respect to a model receptor for nucleic acid components, Askew et al., 1989, *J. Am. Chem. Soc.* 111: 1082-1090: Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elaborating the biological function of the relaxin or relaxin receptor gene product, and for modulating fetal growth. Assays for testing the effectiveness of compounds, identified by, for example, techniques such as those described in Section 5.3.1 through 5.3.3, are discussed, below, in Section 5.3.4.

In Vitro Screening Assays for Compounds that Bind to Relaxin and the Relaxin Receptor In vitro systems may be designed to identify compounds capable of interacting with (e.g., binding to) relaxin and the relaxin receptor (including, but not limited to, the extracellular domain or the cytoplasmic domain of the relaxin receptor). Compounds identified may be useful, for example, in modulating the activity of the wild type and/or mutant relaxin or relaxin receptor gene products; may be useful in elaborating the biological function of relaxin or the relaxin receptor; may be utilized in screens for identifying compounds that disrupt normal relaxin and relaxin receptor interactions; or may in themselves disrupt such interactions.

The principle of the assays used to identify compounds that bind to relaxin or the relaxin receptor involves preparing a reaction mixture of relaxin or the relaxin receptor and the test compound under conditions and for a time sufficient to allow the two components to interact and bind, thus forming a complex which can be detected in the reaction mixture. The screening assays can be conducted in a variety of ways. For example, one method to conduct such an assay would involve anchoring the relaxin or relaxin receptor protein, polypeptide, peptide or fusion protein or the test substance onto a solid phase and detecting relaxin or relaxin receptor/test compound complexes anchored on the solid phase at the end of the reaction. In one embodiment of such a method, the relaxin or relaxin receptor reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for relaxin or the relaxin receptor protein, polypeptide, peptide or fusion protein or the test compound to anchor any complexes formed in solution, and a labeled antibody specific for the other component of the possible complex to detect anchored complexes.

Alternatively, cell-based assays can be used. to identify compounds that interact with relaxin or the relaxin receptor. To this end, cell lines that express relaxin or the relaxin receptor, or cell lines (e.g., COS cells, CHO cells, fibroblasts, etc.) that have been genetically engineered to express relaxin or the relaxin receptor (e.g., by transfection or transduction of relaxin or the relaxin receptor DNA) can be used. Interaction of the test compound with, for example, the relaxin receptor expressed by the host cell can be determined by comparison or competition with native relaxin.

Assays for Intracellular Proteins that Interact with Relaxin and the Relaxin Receptor Any method suitable for detecting protein-protein interactions may be employed for identifying transmembrane proteins or intracellular proteins that interact with relaxin or the relaxin receptor. Among the traditional methods that may be employed are co-immunoprecipitation, crosslinking and co-purification through gradients or chromatographic columns of cell lysates or proteins obtained from cell lysates and relaxin or the relaxin receptor to identify proteins in the lysate that interact with relaxin or the relaxin receptor. For these assays, the relaxin or relaxin receptor component used can be full length, a soluble derivative lacking the membrane-anchoring region (e.g., a truncated relaxin receptor in which the transmembrane segment is deleted resulting in a truncated molecule containing the extra cellular domain fused to the cytoplasmic domain), a peptide corresponding to the cytoplasmic domain or a fusion protein containing relaxin or the cytoplasmic domain of the relaxin receptor. Once isolated, such an intracellular protein can be identified and can, in turn, be used in conjunction with standard techniques, to identify proteins with which it interacts. For example, at least a portion of the amino acid sequence of an intracellular protein that interacts with relaxin or the relaxin receptor can be ascertained using techniques well known to those of skill in the art, such as via the Edman degradation technique. See e.g., Creighton, 1983, *Proteins: Structures and Molecular Principles*, W.H. Freeman and Co., N.Y., pp. 34-49. The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. See, e.g., Ausubel, supra., and *PCR Protocols: A Guide to Methods and Applications*, 1990, Innis, M. et al., eds. Academic Press, Inc., New York.

Additionally, methods may be employed that result in the simultaneous identification of genes that encode transmembrane or intracellular proteins interacting with the relaxin receptor or relaxin. These methods include, for example, probing expression libraries in a manner similar to the well known technique of antibody probing of λgt11 libraries, using labeled relaxin or the relaxin receptor protein, or a relaxin or relaxin receptor polypeptide, peptide or fusion protein, e.g., a relaxin or relaxin receptor polypeptide or a relaxin or relaxin receptor domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One version of this system has been described (Chien et al., 1991, *Proc. Natl. Acad. Sci. USA*, 88:9578-9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a relaxin or relaxin receptor nucleotide sequence encoding relaxin or the relaxin receptor, a relaxin or relaxin receptor polypeptide, peptide or fusion protein, and the other plasmid consists of nucleotides encoding the transcription activator protein's activation domain fused to a cDNA encoding an unknown protein that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, that is detected by an assay for the reporter gene product.

The two-hybrid system or related methodology may be used to screen activation domain libraries for proteins that interact with the "bait" gene product. By way of example, and not by way of limitation, relaxin or the relaxin receptor may be used as the bait gene product. Total genomic or cDNA sequences are fused to the DNA encoding an activation domain. This library and a plasmid encoding a hybrid of a bait relaxin or relaxin receptor gene product fused to the DNA-binding domain are cotransformed into a yeast reporter strain, and the resulting transformants are screened for those that express the reporter gene. For example, and not by way of limitation, a bait relaxin or relaxin receptor gene sequence, such as the open reading frame of relaxin or the relaxin receptor (or a domain of the relaxin receptor), can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait relaxin or the relaxin receptor gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait relaxin or relaxin receptor gene-GAL4 fusion plasmid into a yeast strain that contains a lacZ gene driven by a promoter that contains GAL4 activation sequence. A cDNA encoded protein, fused to GAL4 transcriptional activation domain, that interacts with bait relaxin or relaxin receptor gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait relaxin or relaxin receptor gene-interacting protein using techniques routinely practiced in the art.

Assays for Compounds that Interfere with Relaxin and Relaxin Receptor/Intracellular or Relaxin Receptor/Transmembrane Macromolecule Interactions The macromolecules that interact with relaxin or the relaxin receptor are referred to, for purposes of this discussion, as "binding partners". These binding partners are likely to be involved in the relaxin receptor signal transduction pathway, and therefore, in the role of relaxin or relaxin receptor in the regulation of fetal growth. Therefore, it is desirable to identify compounds that interfere with or disrupt the interaction of such binding partners with relaxin that may be useful in regulating the activity of the relaxin receptor and thus control fetal growth associated with the relaxin receptor activity.

The basic principle of the assay systems used to identify compounds that interfere with the interaction between relaxin or the relaxin receptor and their binding partner or partners involves preparing a reaction mixture containing relaxin or the relaxin receptor protein, polypeptide, peptide or fusion protein as described above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the relaxin or the relaxin receptor moiety and its binding partner. Control reaction mixtures are incubated without the test compound or with a placebo. The formation of any complexes between the relaxin or relaxin receptor moiety and the binding partner is then detected. The formation of a complex in the control reaction, but not in the reaction mixture containing the test compound, indicates that the compound interferes with the interaction of relaxin or the relaxin receptor and the interactive binding partner. Additionally, complex formation within reaction mixtures containing the test compound and normal relaxin or the relaxin receptor protein may also be compared to complex formation within reaction mixtures containing the test compound and a mutant relaxin or relaxin receptor. This comparison may be important in those cases wherein it is desirable to identify compounds that disrupt interactions of mutant but not normal relaxin or relaxin receptors.

The assay for compounds that interfere with the interaction of relaxin or the relaxin receptor and binding partners can be conducted in a heterogeneous or homogeneous format. Heterogeneous assays involve anchoring either the relaxin or relaxin receptor moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance, i.e., by adding the test substance to the reaction mixture prior to or simultaneously with the relaxin or relaxin receptor moiety and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the relaxin or the relaxin receptor moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the relaxin or relaxin receptor gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete; unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface. For example, a labeled antibody specific for the initially non-immobilized species may be used. (The antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected using, for example, an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. In this approach, a preformed complex of the relaxin or relaxin receptor moiety and the interactive binding partner is prepared in which either relaxin or the relaxin receptor or its binding partners is labeled, but the signal generated by the label is quenched due to formation of the complex (e.g., U.S. Pat. No. 4,109,496 by Rubenstein that utilizes this approach for immunoassays). The addition of a test substance that competes with and displaces one of the species from the preformed complex will result in the generation of a signal above background. In this way, test substances that disrupt relaxin or the relaxin receptor/intracellular binding partner interaction can be identified.

In a particular embodiment, a relaxin or relaxin receptor fusion can be prepared for immobilization. For example, the relaxin or relaxin receptor or a peptide fragment, e.g., corresponding to the relaxin receptor cytoplasmic domain, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art. This antibody can be labeled with the radioactive isotope $^{125}$I, for example, by methods routinely practiced in the art. In a heterogeneous assay, e.g., the GST-relaxin receptor fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the relaxin or relaxin receptor gene product and the interactive binding partner can be detected by measuring the amount of radioactivity that remains associated with the glutathione-agarose beads. A successful inhibition of the interaction by the test compound will result in a decrease in measured radioactivity.

Alternatively, the GST-relaxin/relaxin receptor fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the relaxin or relaxin receptor/binding partner interaction can be detected by adding the labeled antibody and measuring the radioactivity associated with the beads.

In another embodiment of the invention, these same techniques can be employed using peptide fragments that correspond to the binding domains of relaxin or the relaxin receptor and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not byway of limitation, a relaxin or relaxin receptor gene product can be anchored to a solid material as described, above, by making a GST-relaxin or -relaxin receptor fusion protein and allowing it to bind to glutathione agarose beads. The interactive binding partner can be labeled with a radioactive isotope, such as $^{35}S$, and cleaved with a proteolytic enzyme such as trypsin. Cleavage products can then be added to the anchored GST-relaxin or -relaxin receptor fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

Assays for Identification of Compounds that Modulate Fetal Growth

Compounds, including, but not limited to, compounds identified via assay techniques such as those described, above, in Sections 5.3.1 through 5.3.3, can be tested for the ability to modulate fetal growth, to treat fetal growth abnormalities, and to treat conditions of placental insufficiency. The assays described above can identify compounds that affect relaxin or relaxin receptor activity (e.g., relaxin receptor agonists or antagonists) or compounds that affect relaxin or relaxin receptor gene activity (by affecting relaxin or relaxin receptor gene expression, including molecules, e.g., proteins or small organic molecules, that affect or interfere with splicing events so that expression of the full length or the truncated form of the relaxin or relaxin receptor can be modulated). However, it should be noted that the assays described can also identify compounds that modulate relaxin or relaxin receptor signal transduction (e.g., compounds that affect downstream signaling events, such as inhibitors or enhancers of tyrosine kinase or phosphatase activities that participate in transducing the signal activated by relaxin binding to the relaxin receptor). The identification and use of such compounds that affect another step in the relaxin or relaxin receptor signal transduction pathway in which the relaxin or relaxin receptor gene and/or gene product is involved and, by affecting this same pathway, modulate the effect of relaxin or the relaxin receptor on the development of fetal growth abnormalities are within the scope of the invention. Such compounds can be used as part of a therapeutic method for modulating fetal growth.

Cell-based systems can be used to identify compounds that may act to modulate fetal growth. Such cell systems can include, for example, recombinant or non-recombinant cells that express relaxin or the relaxin receptor gene. For example, uterine cell lines, primary rat atrial cardiomyocytes, and a monocytic cell line all express the relaxin receptor. These cells can be used without modification if an endogenous component of the relaxin signaling system, such as, for example, relaxin-induced secretion of VEGF from NHE cells, is to be monitored. Alternatively, the cells can be modified by genetic engineering techniques known in the art to provide a convenient reporter system to monitor. In addition, expression host cells (e.g., COS cells, CHO cells, fibroblasts) genetically engineered to express a functional relaxin or relaxin receptor and to respond to activation by the natural relaxin ligand, e.g., as measured by a chemical or phenotypic change, induction of another host cell gene, change in ion flux (e.g., $Ca^{++}$), tyrosine phosphorylation of host cell proteins, etc., can be used as an end point in the assay.

In utilizing such cell systems, cells may be exposed to a compound suspected of exhibiting an ability to modulate fetal growth, at a sufficient concentration and for a time sufficient to elicit such a modulation of fetal growth in the exposed cells. After exposure, the cells can be assayed to measure alterations in the expression of the relaxin or relaxin receptor gene, e.g., by assaying cell lysates—for relaxin or relaxin receptor mRNA transcripts (e.g., by Northern analysis) or for relaxin or relaxin receptor protein expressed in the cell; compounds that regulate or modulate expression of the relaxin or relaxin receptor gene are good candidates as therapeutics. Further, the expression and/or activity of components of the signal transduction pathway of which the relaxin receptor is a part, or the activity of the relaxin receptor signal transduction pathway itself can be assayed.

For example, after exposure, the cell lysates can be assayed for the presence of tyrosine phosphorylation of host cell proteins, as compared to lysates derived from unexposed-control cells. The ability of a test compound to inhibit tyrosine phosphorylation of host cell proteins in these assay systems indicates that the test compound inhibits signal transduction initiated by relaxin receptor activation. The cell lysates can be readily assayed using a Western blot format; i.e., the host cell proteins are resolved by gel electrophoresis, transferred and probed using a anti-phosphotyrosine detection antibody, e.g., an anti-phosphotyrosine antibody labeled with a signal generating compound, such as radiolabel, fluor, enzyme, etc. (e.g., Glenney et al., 1988, *J. Immunol. Methods* 109:277-285; Frackelton et al., 1983, *Mal. Cell. Biol.* 3:1343-1352). Alternatively, an ELISA format could be used in which a particular host cell protein involved in the relaxin receptor signal transduction pathway is immobilized using an anchoring antibody specific for the target host cell protein, and the presence or absence of phosphotyrosine on the immobilized host cell protein is detected using a labeled anti-phosphotyrosine antibody (e.g., King et al., 1993, *Life Sciences* 53:1465-1472). In yet another approach, ion flux, such as calcium ion flux, can be measured as an end point for relaxin receptor stimulated signal transduction.

In addition, animal-based model systems, that may include, for example, transgenic mice lacking the relaxin or relaxin receptor gene, may be used to identify compounds capable of modulating fetal growth in the mice. Such animal models may be used as test substrates for the identification of drugs, pharmaceuticals, therapies and interventions that may be effective in treating fetal growth disorders. For example, animal models may be exposed to a compound suspected of exhibiting an ability to modulate fetal growth, at a sufficient concentration and for a time sufficient to elicit such effects in the exposed animals. The response of the animals to the exposure may be monitored by assessing the growth and/or birth weight of fetuses in treated pregnant animals. Any treatments that affect any aspect of fetal growth should be considered as candidates for human fetal growth modulation. Dosages of test agents may be determined by deriving dose-response curves, as discussed below.

Compounds that Modulate Relaxin or Relaxin Receptor Expression or Activity

Compounds that interact with (e.g., bind to) relaxin or the relaxin receptor (including, but not limited to, the extracellular domain, transmembrane domain, cytoplasmic domain of the relaxin receptor), compounds that interact with (e.g., bind to) intracellular proteins that interact with relaxin or the relaxin receptor (including, but not limited to, the transmembrane and cytoplasmic domain of the relaxin receptor), compounds that interfere with the interaction of relaxin or the relaxin receptor with transmembrane or intracellular proteins involved in relaxin receptor-mediated signal transduction, and compounds that modulate the activity of relaxin or relaxin receptor gene expression or modulate the level of relaxin or the relaxin receptor are capable of modulating fetal growth. More specifically, compounds that increase the levels of relaxin or the relaxin receptor or stimulate the binding of relaxin to the relaxin receptor would cause an increase in fetal growth.

Examples of such compounds are relaxin and relaxin receptor agonists and antagonists. Relaxin receptor antagonist, as used herein, refers to a factor that neutralizes or impedes or otherwise reduces the action or effect of a relaxin receptor. Such antagonists can include compounds that bind relaxin or that bind the relaxin receptor. Such antagonists can also include compounds that neutralize, impede or otherwise reduce the relaxin receptor output, that is, intracellular steps in the relaxin signaling pathway following binding of relaxin to the relaxin receptor, i.e., downstream events that affect relaxin/relaxin receptor signaling, that do not occur at the receptor/ligand interaction level. Relaxin receptor antagonists may include, but are not limited to, proteins, antibodies, small organic molecules or carbohydrates, antibodies that specifically bind relaxin, antibodies that specifically bind relaxin receptor, and compounds that comprise soluble relaxin receptor polypeptide sequences.

For example, relaxin antagonists also include agents, or drugs, that decrease, inhibit, block, abrogate or interfere with binding of relaxin to its receptors or extracellular domains thereof; agents that decrease, inhibit, block, abrogate or interfere with relaxin production or activation; agents that are antagonists of signals that drive relaxin production or synthesis, and agents that prohibit relaxin from reaching its receptor.

Relaxin receptor agonist, as used herein, refers to a factor that activates, induces or otherwise increases the action or effect of a relaxin receptor. Such agonists can include compounds that bind relaxin or that bind the relaxin receptor. Such agonists can also include compounds that activate, induce or otherwise increase relaxin receptor output, that is, intracellular steps in the relaxin signaling pathway following binding of relaxin to the relaxin receptor, i.e., downstream events that affect relaxin/relaxin receptor signaling, that do not occur at the receptor/ligand interaction level. Relaxin receptor agonists may include, but are not limited to proteins, antibodies and antibody fragments, small organic molecules or carbohydrates, relaxin, relaxin analogs, and antibodies that specifically bind and activate relaxin.

Relaxin can also be used in combination with other hormones in the treatment of fetal growth abnormalities. As mentioned above, RLF has synergistic activities when used in combination with relaxin (U.S. Pat. No. 5,911,997). RLF binds specifically to crude membrane preparations of mouse uterus and brain and shows cross-reactivity with a relaxin receptor, but not with an insulin receptor. There may also be unique receptors that interact preferentially with RLF (Büllesbach and Schwabe, 1999, *J. Biol. Chem.* 274:22354-22358). Without intending to be hound by any particular mechanism, the binding of RLF to these receptors may explain the independent and synergistic effects of RLF in various assays and may provide an additional route for modulation of fetal growth by combination therapy using relaxin, RLF, and/or other hormones.

Methods for the Treatment or Prevention of Fetal Growth Abnormalities

Fetal growth abnormalities that can be treated and/or prevented in accordance with the present invention include conditions characterized by fetuses that are small for their gestational age, including, but not limited to intrauterine growth retardation and placental insufficiency. Fetal growth abnormalities that can be treated and/or prevented in accordance with the present invention also include conditions characterized by fetuses that are large for their gestational age, such as in diabetes.

The particular techniques and methods that can be utilized as part of the therapeutic and preventative methods of the invention are presented in detail below.

Restoration or Increase in Relaxin or Relaxin Receptor Expression or Activity to Increase Fetal Growth Any method that increases or activates relaxin or relaxin receptor expression (either transcription or translation), levels, or activity can be used to treat or prevent a condition characterized by fetuses that are small for their gestational age or by placental insufficiency by effectuating an increase in fetal growth or placental size, perfusion, or efficiency. Such approaches can be used to treat or prevent, for example, intrauterine growth retardation.

With respect to an increase in the level of normal relaxin or relaxin receptor gene expression and/or gene product activity, relaxin or relaxin receptor nucleic acid sequences can be utilized to increase fetal growth. Where the cause of the disorder is a defective relaxin or relaxin receptor, treatment can be administered, for example, in the form of gene replacement therapy. Specifically, one or more copies of a normal relaxin or relaxin receptor gene or a portion of the relaxin or relaxin receptor gene that directs the production of a relaxin or relaxin receptor gene product exhibiting normal function, may be inserted into the appropriate cells within a patient or animal subject, using vectors that include; but are not limited to, adenovirus, adeno-associated virus, retrovirus and herpes virus vectors, in addition to other particles that introduce DNA into cells, such as liposomes.

Alternatively, targeted homologous recombination can be utilized to correct the defective endogenous relaxin or relaxin receptor gene in, the appropriate tissue. In animals, targeted homologous recombination can be used to correct the defect in embryonic stem cells in order to generate offspring with a corrected trait.

Additional methods that may be utilized to increase the overall level of relaxin or relaxin receptor gene expression and/or activity include the introduction of appropriate relaxin or relaxin receptor-expressing cells, preferably autologous cells, into a patient at positions and in numbers that are sufficient to increase fetal growth. Such cells may be either recombinant or non-recombinant. The cells can be administered at the anatomical site in the uterus or in the ovaries, or as part of a tissue graft located at a different site in the body. Such cell-based gene therapy techniques are well known to those skilled in the art, e.g., Anderson, et al., U.S. Pat. No. 5,399,349; Mulligan and Wilson, U.S. Pat. No. 5,460,959.

Finally, compounds, identified in the assays described above, that stimulate or enhance the signal transduced by activated relaxin receptor, e.g., by activating downstream signaling proteins in the relaxin receptor cascade and thereby by-passing the defective relaxin receptor, can be used to increase fetal growth. The formulation and mode of administration will depend upon the physico-chemical properties of the compound.

Inhibition of Relaxin or Relaxin Receptor Expression, Levels or Activity to Decrease Fetal Growth Any method that neutralizes, slows or inhibits relaxin or relaxin receptor expression (either transcription or translation), levels, or activity can be used to treat or prevent a condition characterized by fetuses that are large for their gestational age by effectuating a decrease in fetal growth.

For example, the administration of compounds such as soluble peptides, proteins, fusion proteins, or antibodies (including anti-idiotypic antibodies) that bind to and "neutralize" circulating relaxin, the natural ligand for the relaxin receptor, can be used to effectuate a decrease in fetal growth. To this end, peptides corresponding to the extracellular domain of the relaxin receptor, soluble deletion mutants of the relaxin receptor, or either of these relaxin receptor domains or mutants fused to another polypeptide (e.g., an IgFc polypeptide) can be utilized. Alternatively, anti-idiotypic antibodies or Fab fragments of anti-idiotypic antibodies that mimic the relaxin receptor extracellular domain and neutralize relaxin can be used. For treatment, such relaxin receptor peptides, proteins, fusion proteins, anti-idiotypic antibodies or Fabs are administered to a subject in need of treatment at therapeutically effective levels. For prevention, such relaxin receptor peptides, proteins, fusion proteins, anti-idiotypic antibodies or Fabs are administered to a subject at risk for high fetal growth rate, for a time and concentration sufficient to prevent the high fetal growth rate.

In an alternative embodiment for neutralizing circulating relaxin, cells that are genetically engineered to express soluble peptides, proteins, fusion proteins, or antibodies (including anti-idiotypic antibodies) that bind to and "neutralize" circulating relaxin may be administered to a patient, whereupon they will serve as "bioreactors" in vivo to provide a continuous supply of the relaxin-neutralizing protein. Such cells may be obtained from the patient or an MHC compatible donor and can include, but are not limited to, fibroblasts, blood cells (e.g., lymphocytes), adipocytes, muscle cells, endothelial cells etc. The cells are genetically engineered in vitro using recombinant DNA techniques to introduce the coding sequence for the desired relaxin-neutralizing protein into the cells, e.g., by transduction (using viral vectors, and preferably vectors that integrate the transgene into the cell genome) or transfection procedures, including, but not limited to, the use of plasmids, cosmids, YACs, electroporation, liposomes, etc. The relaxin-neutralizing protein coding sequence can be placed under the control of a strong constitutive or inducible promoter or promoter/enhancer to achieve expression and secretion of the peptide or protein. The engineered cells that express and secrete the desired gene product can be introduced into the patient systemically, e.g., in the circulation, intraperitoneally, at the choroid plexus or hypothalamus. Alternatively, the cells can be incorporated into a matrix and implanted in the body, e.g., genetically engineered fibroblasts can be implanted as part of a skin graft; genetically engineered endothelial cells can be implanted as part of a vascular graft. For example, see Anderson et al. U.S. Pat. No. 5,399,349; and Mulligan and Wilson, U.S. Pat. No. 5,460,959 each of which is incorporated by reference herein in its entirety.

When the cells to be administered are non-autologous cells, they can be administered using well known techniques that prevent the development of a host immune response against the introduced cells. For example, the cells may be introduced in an encapsulated form which, while allowing for an exchange of components with the immediate extracellular environment, does not allow the introduced cells to be recognized by the host immune system.

In an alternate embodiment, therapies that modulate fetal growth can be designed to reduce the level of endogenous relaxin or relaxin receptor gene expression, e.g., using antisense or ribozyme approaches to inhibit or prevent translation of relaxin or relaxin receptor mRNA transcripts; triple helix approaches to inhibit transcription of the relaxin or relaxin receptor gene; or targeted homologous recombination to inactivate or "knock out" the relaxin or relaxin receptor gene or its endogenous promoter. The antisense, ribozyme or DNA constructs described herein could be administered systemically or could be administered directly to the site containing the cells that express the targeted gene.

Antisense approaches involve the design of oligonucleotides (either DNA or RNA) that are complementary to relaxin or relaxin receptor mMA. The antisense oligonucleotides will bind to the complementary relaxin or relaxin receptor mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The skilled artisan recognizes that modifications of gene expression, can be obtained by designing antisense molecules to the control regions of the relaxin or relaxin receptor genes, i.e. promoters, enhancers, and introns, as well as to the coding regions of these genes. Such sequences are referred to herein as relaxin-encoding polynucleotides or relaxin receptor-encoding polynucleotides, respectively.

Oligonucleotides derived from the transcription initiation site, e.g. between −10 and +10 regions of the leader sequence, are preferred. Oligonucleotides that are complementary to the 5' end of the message, e.g., the 5' untranslated sequence up to and including the AUG initiation codon, generally work most efficiently at inhibiting translation. However, sequences complementary to the 3' untranslated sequences of mRNAs have recently been shown to be effective at inhibiting translation of mRNAs as well. See generally, Wagner, 1994, *Nature* 372: 333-335. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of the relaxin or relaxin receptor mRNA, antisense nucleic acids should be at least six nucleotides in length, and are preferably oligonucleotides ranging from 6 to about 50 nucleotides in length. In specific aspects the oligonucleotide is at least nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (e.g., as taught in Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO88/09810, published Dec. 15, 1988) or the blood-brain barrier (e.g., PCT Publication No. WO89/10134, published Apr. 25, 1988), hybridization-triggered cleavage agents (e.g., Krol et al., 1988, *BioTechniques* 6:958-976) or intercalating agents (e.g., Zon, 1988, *Pharm. Res.* 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety that is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, *Nucl. Acids Res.* 15:6625-6641). The oligonucleotide is a 2'-O-methylribonucleotide (Inoue et al., 1987, *Nucl. Acids Res.* 15:6131-6148), or a chimeric RNA-DNA analogue (Inoue et al., 1987, *FEBS Lett.* 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al., 1988, *Nucl. Acids Res.* 16:3209, and methylphosphonate oligonucleotides can be prepared by use of controlled pore glass polymer supports (Sarin et al., 1988, *Proc. Natl. Acad. Sci. USA* 85:7448-7451).

While antisense nucleotides complementary to the relaxin or relaxin receptor coding region sequence could be used, those complementary to the transcribed untranslated region are most preferred.

The antisense molecules should be delivered to cells that express the relaxin or relaxin receptor gene in vivo. A number of methods have been developed for delivering antisense DNA or RNA to cells. For example, antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

A preferred approach for achieving intracellular concentrations of the antisense sufficient to suppress translation of endogenous mRNAs utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous relaxin or relaxin receptor transcripts and thereby prevent translation of the relaxin or relaxin receptor mRNA, respectively. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods which are standard in the art. Vectors can be plasmid, viral, or other vectors known in the art which are used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. USA 78:1441-1445), the regulatory sequences of the metallothionein gene (Brinster et al., 1982, Nature 296:39-42), etc. Any type of plasmid, cosmid, YAC or viral vector can be used to prepare the recombinant DNA construct that can be introduced directly into the tissue site, e.g., the choroid plexus or hypothalamus. Alternatively, viral vectors can be used that selectively infect the desired tissue (e.g., herpes virus vectors may be used for infecting brain tissue), in which case administration may be accomplished by another route (e.g., systemically).

Ribozyme molecules-designed to catalytically cleave relaxin or relaxin receptor mRNA transcripts can also be used to prevent translation of relaxin or relaxin receptor mRNA and expression of relaxin or the relaxin receptor. See, e.g., PCT International Publication WO90/11364, published Oct. 4, 1990; Sarver et al., 1990, Science 247:1222-1225. While ribozymes that cleave mRNA at site specific recognition sequences can be used to destroy relaxin or relaxin receptor mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the at and is described more fully in Haseloff and Gerlach, 1988, Nature, 334:585-591. There are typically hundreds of potential hammerhead ribozyme cleavage sites within any given gene sequence. See, e.g., U.S. Pat. No. 5,972,621. Preferably, the ribozyme is engineered so that the cleavage recognition site is located near the 5' end of the relaxin or relaxin receptor mRNA to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zang, et al., 1984, Science, 224:574-578; Zaug and Cech, 1986, Science, 231:470-475; Zaug, et al., 1986, Nature, 324: 429-433; published International patent-application No. WO 88/04300 by University Patents Inc.; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences that are present in the relaxin and relaxin receptor mRNA targets.

As in the antisense approach, the ribozymes can be composed of modified oligonucleotides (e.g., for improved stability, targeting, etc.) and should be delivered to cells that express relaxin and the relaxin receptor in vivo. A preferred method of delivery involves using a DNA construct "encoding" the ribozyme under the control of a strong constitutive pol III or pol II promoter, so that transfected cells will produce sufficient quantities of the ribozyme to destroy endogenous relaxin and relaxin receptor messages and inhibit translation. Because ribozymes, unlike antisense molecules, are catalytic, a lower intracellular concentration is required for efficiency.

Similarly, relaxin or relaxin receptor inhibition can be achieved by using "triple helix" base-pairing methodology. Triple helix pairing compromises the ability of the double helix to open sufficiently for the binding of polymerases, transcription factors, or regulatory molecules. Techniques for utilizing triple helix technology are well known to those of skill in the art. See generally Helene, 1991, Anticancer Drug Des. 6:569-84; Helene, 1992, Ann. N.Y. Acad. Sci. 660:27-36; and Maher, 1992, Bioassays 14:807-15.

Endogenous relaxin or relaxin receptor gene expression can also be reduced by inactivating or "knocking out" the relaxin or relaxin gene or its promoter using targeted homologous recombination. See, e.g., Smithies et al., 1985, Nature 317:230-234; Thomas and Capecchi, 1987, Cell 51:503-512; Thompson et al., 1989, Cell 5:313-321; each of which is incorporated by reference herein in its entirety. For example, a mutant, non-functional relaxin or relaxin receptor (or a completely unrelated DNA sequence) flanked by DNA homologous to the endogenous relaxin or relaxin receptor gene (either the coding regions or regulatory regions) can be used, with or without a selectable marker and/or a negative selectable marker, to transfect cells that express relaxin or relaxin receptor in vivo. Insertion of the DNA construct, via targeted homologous recombination, results in inactivation of the relaxin or relaxin receptor gene. Such approaches are particularly suited in the veterinary field where modifications to embryonic stem cells can be used to generate animal offspring with an inactive relaxin receptor (e.g., Thomas and Capecchi 1987 and Thompson; 1989, supra). However, this approach can be adapted for use in humans provided the recombinant DNA constructs are directly administered or targeted to the required site in vivo using appropriate viral vectors.

Alternatively, endogenous relaxin or relaxin receptor gene expression can be reduced by targeting deoxyribonucleotide sequences complementary to the regulatory region of the relaxin or relaxin receptor gene (i.e., promoters and/or enhancers) to form triple helical structures that prevent transcription of the relaxin or relaxin receptor gene in target cells in the body. See, e.g., Helene, 1991, Anticancer Drug Res., 6:569-84; Helene et al., 1992, Ann. N.Y. Acad. Sci. 660:27-36; and Maher, 1992, Bioassays 14:807-15.

In yet another embodiment of the invention, the activity of relaxin or the relaxin receptor can be reduced using a "dominant negative" approach to effectuate a decrease in fetal growth. To this end, constructs that encode a defective relaxin or relaxin receptor can be used in gene therapy approaches to diminish the activity of the relaxin or relaxin receptor in appropriate target cells. For example, nucleotide sequences that direct host cell expression of relaxin receptors in which the cytoplasmic domain or a portion of the cytoplasmic domain is deleted or mutated can be introduced into cells in uterine tissue (either by in vivo or ex vivo gene therapy methods described above). Alternatively, targeted homologous recombination can be utilized to introduce such deletions or mutations into the subject's endogenous relaxin receptor gene in the uterus. The engineered cells will express non-functional receptors (i.e., an anchored receptor that is capable of binding its natural ligand, but incapable of signal transduction). Such engineered cells present in the uterus should demonstrate a diminished response to the endogenous relaxin ligand and result in decreased fetal growth.

An additional embodiment of the present invention is a method to decrease relaxin levels by increasing breakdown of the relaxin protein, i.e., by binding of an antibody such that the relaxin protein is targeted for removal. An alternative embodiment of the present invention is a method to decrease relaxin receptor levels by increasing the breakdown of the relaxin receptor protein, i.e., by binding of an antibody such that the relaxin receptor protein is targeted for removal. Another embodiment is to decrease relaxin levels by increasing the synthesis of a soluble form of the relaxin receptor, that binds to free relaxin.

Another embodiment of the present invention is a method to administer compounds that affect relaxin receptor structure or function. Such compounds include, but are not limited to, proteins, nucleic acids, carbohydrates or other molecules that upon binding alter relaxin receptor structure or function and thereby render the receptor ineffectual in its activity.

Gene Therapy Approaches to Controlling Relaxin and Relaxin Receptor Activity and Treating or Preventing Fetal Growth Abnormalities The expression of relaxin and the relaxin receptor can be controlled in vivo (e.g. at the transcriptional or translational level) using gene therapy approaches to regulate relaxin and relaxin receptor activity and treat fetal growth abnormalities. Certain approaches are described below.

With respect to an increase in the level of normal relaxin and relaxin receptor gene expression and/or relaxin and relaxin receptor gene product activity, relaxin and relaxin receptor nucleic acid sequences can be utilized for the treatment of fetal growth abnormalities. Where the cause of the fetal growth abnormality is a defective relaxin or rela4n receptor gene, treatment can be administered, for example, in the form of gene replacement therapy. Specifically, one or more copies of a normal relaxin or relaxin receptor gene or a portion of the gene that directs the-production of a gene product exhibiting normal function, may be inserted into the appropriate cells within a patient or animal subject, using vectors which include, but are not limited to adenovirus, adeno-associated virus, retrovirus and herpes virus vectors, in addition to other particles that introduce DNA into cells, such as liposomes.

Targeted homologous recombination can be utilized to correct the defective endogenous relaxin or relaxin receptor gene in the appropriate tissue; e.g., ovarian and uterine tissue, respectively. In animals, targeted homologous recombination can be used to correct the defect in embryonic stem cells in order to generate offspring with a corrected trait.

Additional methods which may be utilized to increase the overall level of relaxin or relaxin receptor gene expression and/or activity include the introduction of appropriate relaxin- or relaxin receptor-expressing cells, preferably autologous cells, into a patient at positions and in numbers which are sufficient to ameliorate the symptoms of fetal growth abnormalities, including, but not limited to, IUGR. Such cells may be either recombinant or non-recombinant. Among the cells which can be administered to increase the overall level of relaxin or relaxin receptor gene expression in a patient are normal cells, or ovarian or uterine cells that express the relaxin or relaxin receptor gene, respectively. The cells can be administered at the anatomical site in the ovary of in the uterus, or as part of a tissue graft located at a different site in the body. Such cell-based gene therapy techniques are well known to those skilled in the art, e.g., Anderson, et al., U.S. Pat. No. 5,399,349; Mulligan and Wilson, U.S. Pat. No. 5,460,959.

Pharmaceutical Formulations and Methods of Treating Fetal Growth Abnormalities

The compounds of this invention can be formulated and administered to inhibit a variety of fetal growth abnormality by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a therapeutically effective amount of the compound sufficient to result in amelioration of symptoms of the fetal growth abnormality and will, of course, vary depending upon known factors such as the pharmacodynamic characteristics of the particular active ingredient and its mode and route of administration; age, health and weight of the recipient; nature and extent of symptoms; kind of concurrent treatment, frequency of treatment and the effect desired.

Dose Determinations

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{10}$ (the dose therapeutically effective in 50% of the population). The dose ratio between toxic and therapeutic effects is therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells; and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Specific dosages may also be utilized for antibodies. Typically, the preferred dosage is 0.1 mg/kg to 100 mg/kg of body weight (generally 10 mg/kg to 20 mg/kg), and if the antibody is to act in the brain, a dosage of 50 mg/kg to 100 mg/kg is usually appropriate. If the antibody is partially human or fully human, it generally will have a longer half-life within the human body than other antibodies. Accordingly, lower dosages of partially human and fully human antibodies is often possible. Additional modifications may be used to further stabilize antibodies. For example, lipidation can be used to stabilize antibodies and to enhance uptake and tissue penetration (e.g., into the brain). A method for lipidation of antibodies is described by Cruikshank et al., (1997), *J. Acquired Immune Deficiency Syndromes and Human Retrovirology* 14:193).

A therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

Moreover; treatment of a subject with a therapeutically effective amount of a protein, polypeptide or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5 or 6 weeks.

The present invention further encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including hetero-organic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in *Remington's Pharmaceutical Sciences*, a standard reference text in this field.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly(lactic acid) or ethylenevinylacetate copolymers. In addition to being incorporated, these agents can also be used to trap the compound in microcapsules.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Useful pharmaceutical dosage forms, for administration of the compounds of this invention can be illustrated as follows:

Capsules: Capsules are prepared by filling standard two-piece hard gelatin capsulates each with the desired amount of powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing the desired amount of the active ingredient. The capsules are then washed and dried.

Tablets: Tablets are prepared by conventional procedures so that the dosage unit is the desired amount of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

Gene Therapy Administration: Where appropriate, the gene therapy vectors can be formulated into preparations in solid, semisolid, liquid or gaseous forms such as tablets, capsules, powders, granules, ointments, solutions, suppositories, injections, inhalants, and aerosols, in the usual ways for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds.

Accordingly, the pharmaceutical composition of the present invention may be delivered via various routes and to various sites in an animal body to achieve a particular effect (see, e.g., Rosenfeld et al., 1991, supra; Rosenfeld et al., 1991, *Clin. Res.*, 3 9(2), 31 1A, 1991; Jaffe et al.; supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The composition of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

Accordingly, the present invention also provides a method of transferring a therapeutic gene to a host, which comprises administering the vector of the present invention, preferably as part of a composition, using any of the aforementioned routes of administration or alternative routes known to those skilled in the art and appropriate for a particular application. The "effective amount" of the composition is such as to produce the desired effect in a host which can be monitored using several end-points known to those skilled in the art. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of adenoviral receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

The following examples are offered by way of example, and are not intended to limit the scope of the invention in any manner.

EXAMPLE 1

The effect of relaxin administration on tissues thought to be targeted by relaxin during pregnancy and on the health and well-being of neonates born to mothers treated with relaxin was tested in female marmoset monkeys. Relaxin was administered during the period that spanned ovulation, implantation, and early pregnancy of the monkeys.

Animals. Female marmosets (*Callithrix jacchus*) were young, healthy breeders in a captive breeding colony and were housed in pairs with males under controlled environmental conditions. Under these conditions, pregnancy occurs in 90% of receptive females per cycle. Animal weights and general health were recorded immediately prior to the start of the study.

Relaxin. The recombinant human relaxin used in the study is identical to the naturally occurring, mature product of the human relaxin H2 gene and contains a 24 residue A chain and a 29 residue B chain. It was used at a concentration of either 1.5 mg/mL or 5.0 mg/mL and was formulated in 20 mM sodium acetate, pH 5.0 as a vehicle. Control animals received either vehicle alone or Ringer's saline solution.

Treatment methods. Luteal regression was induced to control mating cycles in female marmosets by intramuscular injection of PGF2α (0.8 μg) on day 12 of the luteal phase (Summers et al., 1985, *J Reprod. Fert.* 73:133-138). The day of PGF2α injection was considered to be day 1 of the 34-day study. Two monkeys were treated by continuous subcutaneous infusion of relaxin (12 μg/kg/day at 0.25 μL/hr) via an implanted 28-day osmotic pump (Alzet, model #2004; 3.0 cm×0.7 cm; Alza Corp., Palo Alto, Calif.). One control monkey was treated in an identical manner with vehicle/saline. Treatment was begun on day 4 of the study and was continued for 28 days. The treatment thus spanned the period from just prior to ovulation until 10-12 days post-implantation of the embryo. The dosage was chosen in an attempt to achieve circulating levels of relaxin of 2 ng/mL, a level that is approximately two-fold that measured during the peri-implantation period and early pregnancy in the marmoset (A. Einspanier, personal communication; Steinetz et al., 1995, *Biol. Reprod.* 53:834-839) and in humans (Stewart et al., 1990, *J. Clin. Endocrin. Metab.* 70:1771-1773). Pumps were implanted subcutaneously in the back of the neck under ketamin/atropine/rompun anesthesia. The subjects were isolated from contact with males for one to two days to allow healing to occur. Two additional monkeys were treated by twice-daily intramuscular injection of relaxin (48 ng/kg/day). An additional control monkey was treated by twice-daily intramuscular injection of vehicle/saline.

Endometrial thickness was measured by ultrasonography three times during the dosing period and once at two days subsequent to the dosing. During lactation, the ability of the neonates to suckle normally was noted, as was uterine involution.

Transabdominal ultrasound examination was performed on unsedated and unshaved animals using an ESAOTE ultrasound system fitted with mechanical probes of 7.5 and 10 MHz (Oerke et al., 1995, *Am. J. Primatol.* 36:1-13; Oerke et al., 1996, *Am. J. Primatol.* 39:99-113).

Results. All six female marmosets became pregnant during the mating cycle in which treatment was given. The animals treated with relaxin were found to have substantially thicker endometrial tissues than controls (FIG. 1 and Table I. Birth of the offspring was uneventful in three of the four marmosets receiving relaxin and in both marmosets receiving vehicle. The number of offspring per dam was two or three, which is normal for this species in this colony. The relaxin-treated marmosets gave birth to offspring having substantially higher birth weights than animals treated with vehicle alone (Table II). Although the offspring of one of the dams died in utero at the end of the gestation period and were removed by Caesarian section for examination, their mortality was attributed to the inability of the presumptive first-born to pass through the birth canal because of its large size. This dam delivered during the early morning and was unattended during labor. It is likely that had she been discovered earlier, the offspring could have been rescued by Caesarian section. The three babies appeared normal by visual inspection, albeit larger than usual for this species, and a standard autopsy revealed no congenital abnormalities. The mother recovered fully and underwent milk ejection, as well as uterine involution, normally.

TABLE I

| | | | Endometrial thickness* | | | |
|---|---|---|---|---|---|---|
| Test Article | Animal No. | Route | Endometrial Thickness Day 10 (cm) | Endometrial Thickness Day 14 (cm) | Endometrial Thickness Day 18 (cm) | Endometrial Thickness Day 34 (cm) |
| Vehicle | W215 | i.m. | 0.10 | 0.10 | 0.13 | 0.15 |
| Vehicle | W89 | s.c. | 0.10 | 0.10 | 0.12 | 0.15 |
| rhRLX | W211 | s.c. | 0.10 | 0.20 | 0.25 | 0.30 |
| rhRLX | W237 | i.m. | 0.10 | 0.25 | 0.30 | 0.33 |
| rhRLX | W111 | s.c. | 0.19 | 0.22 | 0.30 | 0.35 |
| rhRLX | W216 | i.m. | 0.12 | 0.20 | 0.30 | 0.32 |

*Endometrial thickness was measured by ultrasonography.

Endometrial thickness was too thin to be quantified by ultrasonography on Day 6, and this timepoint is not included in this table.

TABLE II

Number of live births, gestation length, neonatal birth weight

| Test Article | Animal No. | Route | Live births/Fetuses (#/#)* | Gestation Length (d) | Birth weight (g) | Mean birth weight (g) |
|---|---|---|---|---|---|---|
| Vehicle | W215 | i.m. | 2/2 | 145 | 29.7; 31.0 | 30.4 ± 0.9 |
| Vehicle | W89 | s.c. | 3/3 | 142 | 29.2; 30.3; 32.4 | 30.6 ± 1.6 |
| Relaxin | W211 | s.c. | 3/3 | 137 | 34.3; 35.2; 37.1 | 35.5 ± 1.4 |
| Relaxin | W237 | i.m. | 0/3** | 142 | 35.3; 36.5; 36.9 | 36.2 ± 0.8 |
| Relaxin | W111 | s.c. | 3/3 | 135 | 35.2; 35.7; 36.2 | 35.7 ± 0.5 |
| Relaxin | W216 | i.m. | 3/3 | 137 | 34.9; 35.5; 36.2 | 35.5 ± 0.7 |

*Number of fetuses/Number of gestational sacs at Day 34.
**Mortality of triplets attributed to inability of presumptive firstborn to pass through the birth canal.

EXAMPLE 2

The effect of relaxin administration on (1) tissues thought to be targeted by relaxin during pregnancy and (2) on the health and well-being of neonates born to mothers treated with relaxin was tested in the female Old World cynomolgus monkey, *Macaca fascicularis*. Endocrine signals and the timing of implantation in these monkeys are quite similar to that seen in humans. Ovarian hormone production during the luteal phase of the cycle is similar in the macaque and humans, and both cycles end with sloughing of the endometrium. Relaxin levels in the circulation during the luteal phase and peri-implantation period approximate 50 pg/mL and 40 pg/mL in humans and macaques, respectively. Implantation occurs nine days after fertilization in the macaque while it occurs approximately two days earlier in humans, but trophoblast rescue of the corpus luteum occurs similarly in both species with increased chorionic gonadotropin production three days after implantation. Enhanced relaxin and progesterone release by the corpus luteum, as well as increased estrogen secretion by the ovary, occurs in response to conception in both *M. fascicularis* and humans. Relaxin levels approximating 1 ng/mL have been reported in pregnant females in both species. Finally, the relaxin receptor, LGR7, has been detected in the endometrium of both the human and the cynomolgus monkey.

The vagaries of mating and natural conception in macaques that would make the study of implantation and early pregnancy difficult can be circumvented by the use of in vitro fertilization (IVF) and embryo transfer (ET) techniques. Previous studies have shown some success in *M. fascicularis*, with implantation rates of 8.3-12.0% having been achieved using 1-4 fresh or frozen-thawed embryos transferred per recipient into natural cycles. The present study uses more recently developed techniques (see, e.g., Trounson A O et al., *Med. J. Aust.*, 1993, 158: 853; Zelinski-Wooten M B et al., *Hum. Reprod.*, 1995, 10: 1658-1666; Shaw J M et al., "Cryopreservation of oocytes and embryos," In: Trounson A O and Gardner D K (eds.), *Handbook of In Vitro Fertilization*, CRC Press, Boca Raton; 2000: 373-412; Trounson A O et al., *J Reprod Fertil.*, 1982, 64: 285-294).

Materials and Methods

Except where otherwise indicated chemicals were obtained from Sigma Chemical Co. (St. Louis, Mo., USA). All experimental procedures were conducted at Monash University embryology facilities located at Bogor Agricultural University, Bogor, Indonesia. Experiments were approved by the Institutional Animal Care and Use Committee at Bogor Agricultural University (National Institutes of Health approval number A5287-01). Male and female animals were anesthetized with ketamine (25 mg/kg, IM) in combination with pre- and post-operative analgesia; Ketoprofen (7.5 mg/kg, IM) and Butorphanol (0.15 mg/kg, IM).

Oocyte collection and Preparation

Sexually mature *M. fascicularis* females were monitored for regularity of three cycles prior to oocyte collection. Oocyte donors were subjected to ovarian superovulation with recombinant human follicle stimulating hormone (rhFSH, 60 IU/day IM; Serono Pty Ltd, Sydney, NSW, Australia), starting two days after the beginning of menses and continuing for 11 to 13 days. Follicular maturation was completed with administration of human chorionic gonadotrophin (urinary hCG, 1000 IU IM; Serono Pty Ltd, Sydney, Australia) the day following the last FSH administration. Ovarian development was monitored by ultrasound (5.0 MHz transabdominal curved array probe; Sonosite, Bothell, Wash., USA). Oocytes were retrieved from anesthetized animals at laparotomy 28-30 hours following hCG administration. Follicles were aspirated at a negative pressure of 120 to 125 mmHg using sterile ovum aspiration kits (Cook IVF, Brisbane, QLD, Australia).

Harvested oocytes were treated with hyaluronidase (80 IU/ml) to remove expanded cumulus cell populations and classified according to nuclear maturation status (germinal vesicle, GV; Metaphase I, MI; Metaphase II, MII). MII oocytes were placed into micro drops (50 µl) of human tubal fluid culture medium (HTF, Chemtec Pty Ltd, VIC, Australia), supplemented with 3.0 mg/ml bovine serum albumin (HTF+BSA), and overlaid with mineral oil. Oocytes were allowed to rest in culture medium for 4 to 6 hours after collection prior to IVF.

Sperm Collection and Preparation

Epididymal sperm was collected from 16 anesthetized males by needle biopsy and transferred into HEPES-buffered human tubal fluid (mHTF, Chemtec Pty Ltd, Melbourne, VIC, Australia), supplemented with 3.0 mg/ml bovine serum albumin (mHTF+BSA). Sperm were washed in mHTF+BSA and centrifuged for 10 minutes at 700 g. The supernatant was discarded and the sperm pellet was overlaid with fresh mHTF+BSA. A motile sperm-rich fraction was obtained by allowing sperm to swim up into fresh mHTF+BSA for 15 minutes. Motile sperm were transferred to HTF+BSA in an atmosphere of 5% CO2 in air at 37° C., and subjected to activation with dibutyryl-cAMP (0.1 mM) and caffeine (0.5-1.0 mM) for 60 minutes prior to use for IVF.

In Vitro Fertilization and Embryo Freezing

Oocytes were fertilized in vitro by adding aliquots of hyperactivated sperm (final concentration 250,000 motile sperm/mL) to MII oocytes. Oocytes were incubated in the presence of sperm for 12 to 15 hours in an atmosphere of 5% CO2 in air prior to transfer into fresh HTF+BSA. Fertilization was recorded as the presence of two pronuclei and second polar body extrusion. Zygotes were cultured in vitro in HTF+BSA at 37° C. in an atmosphere of 5% CO2, 5% $O_2$ and 90% N2. Embryos reaching the 4- and 8-cell stages of development were frozen, according to methods described previously (Shaw J M et al., in: Trounson A O and Gardner D K (eds.), *Handbook of In Vitro Fertilization*, CRC Press, Boca Raton; 2000: 373-412), so that embryo transfers could be timed to the expected window of ovulation of recipient females. Briefly, embryos were initially placed into phosphate-buffered saline, supplemented with 4 mg/ml BSA (PBS+BSA) for 10 minutes at room temperature. Embryos were then transferred to a solution containing 1.5 M 1,2-propanediol (PrOH) in PBS+BSA for a further 10 minutes. Embryos were then transferred into a solution containing 1.5 M PrOH and 0.1 M sucrose in PBS+BSA, and immediately loaded into pre-rinsed 0.25 cc freezing straws (two embryos per straw). Straws containing embryos were heat-sealed and transferred to a controlled-rate freezing machine with a starting temperature of 20° C. Embryos were cooled at −2° C. per min to −6° C., and seeded. After being held at −6° C. for 10 min, embryos were cooled at −0.3° C. per min to −40° C., then plunged directly into liquid nitrogen and stored.

Embryo Recipients and Embryo Transfer

Recipient females were monitored for regularity of three cycles prior to embryo transfer and randomized to two groups prior to osmotic pump implantation. Pumps (Model 2004, Alza Corporation, Palo Alto, Calif., USA) were used for delivery of rhRLX (Lot 63601, Connetics Corporation, Palo Alto, Calif., USA), at a dose of 8 μg/kg/day, or vehicle alone (25 mM acetate, pH 5.5) for 21 days. The rhRLX dose was selected on the basis of previously conducted clinical studies in humans (Seibold J R et al., *J. Rheumatol.* 1998; 25: 302-307) as well as a small pharmacokinetic study in cynomolgus monkeys, which confirmed that this dose would result in steady state circulating relaxin levels of 1-2 ng/ml (data not shown). These levels approximate concentrations observed in pregnant women and macaques, which range from 0.03 ng/ml during the early luteal phase to 1.0 ng/ml during early pregnancy. Pumps were loaded and were primed at 37° C., according to manufacturer's instructions. Proper loading of osmotic pumps was verified by weighing, according to manufacturers instructions (mean fill efficiency of 98.9±0.8% was achieved).

Pumps were implanted (Day 0) subcutaneously on the backs of recipient monkeys, under anesthesia, seven days prior to embryo transfer (Day 7). Eleven females were dosed with relaxin and eleven received vehicle alone. Embryos produced through IVF were thawed according to established methods (Balmaceda J P et al., *Fertil. Steril.*, 1986; 45: 403-406) and placed in culture medium (HTF-BSA) prior to embryo transfer. Four viable embryos (>50% blastomere survival post-thaw) were transferred to each of the 22 recipient females during the expected ovulation window in a natural cycle (days 13-17), which has been described previously (Dukelow W R et al., *J. Med. Primatol.* 1979; 8:39-47). Briefly, the day of ovulation (DO) to cycle length (CL) ratio (DO/CL) was used to identify the expected midpoint of the ovulation window, to which two days were added to determine the date of embryo transfer. Embryos were transferred at laparotomy through the fimbria into the mid-ampullary region of each fallopian tube (n=2/oviduct) using sterile embryo transfer catheters (Cook IVF, Brisbane, QLD, Australia). Some of the thawed embryos were analyzed for development in vitro following culture in HTF-BSA.

Endometrial Thickness and Embryo Implantation

The effects of systemic exposure to exogenous, highly purified, recombinant human relaxin, during the peri-implantation period, on implantation, pregnancy rates, endometrial function, and placental growth were measured. Endometrial variables were assessed and analysed by an individual (E.H.) blinded to the treatment groups. Endometrial thickness was monitored by ultrasound (5.0 MHz transabdominal curved array probe; Sonosite, Bothell, Wash., USA) in transverse and sagittal planes on Days 0, 7, 21, and 28 following pump implantation. Assessments were considered reliable when two measurements could be obtained in each plane. Measurements in both planes were used for statistical analysis, and mean values reported in the results. The number of gestational sacs and fetuses were recorded at Days 21, and 28 and 67. Placental size (circumference and surface area) was also monitored by ultrasound at Day 67. Pregnancies were terminated following the Day 67 determination of placental size.

Implantation rate per treatment group was reported as the number of embryos implanted/total number of embryos transferred; in this study, the total number of embryos transferred per treatment group was 44. Pregnancy rate was expressed as the percentage of pregnant recipients/total number of recipients. Multiple pregnancy rate was expressed as the percentage of multiple gestations/number of pregnant recipients.

Implantation bleeding, or placental sign, a phenomenon associated with embryonic implantation in non-human primates, was quantified by monitoring the first day of observance of bleeding sign (start) and the total number of days of visible vaginal bleeding following embryo transfer (total) in relaxin-and vehicle-treated pregnancies. Menses, which occurred when embryo transfer did not result in a pregnancy, was also calculated as the number of days of visible vaginal bleeding.

Serum Hormone Analysis

Serum rhRLX levels were measured by quantitative ELISA specific for human relaxin (H2), as reported in detail in Danielson L et al., *J. Clin. Invest.*, 1999; 103: 525-533. Samples were initially diluted 1:2 and compared against a standard curve (11.72 to 750 pg/ml, n=7, r=0.99, t=161.5, $P<0.0001$). Samples that produced readings that were above the standard curve were diluted 1:10 and run a second time. Concentrations were corrected for dilution factor. Intra- and inter-assay coefficients of variation were 4.2% and 7.2%, respectively. Serum hormone values were log transformed prior to statistical analysis. Analyses performed prior to this study demonstrated that cynomolgus monkey relaxin at levels observed during normal pregnancy (~1 ng/mL) were below the limit of detection in this assay (data not shown).

Data Analysis

Data for endometrial thickness, implantation bleeding, and placental sizes (circumference and surface area) were expressed as mean±the standard error of the mean (SEM; n=4-11 animals). Significance of treatment effects on endometrial thickness or serum relaxin levels was assessed by Student's t-test following two-way ANOVA with one repeated measure (Zar J H, *Biostatistical analysis*, Prentice Hall, New Jersey; 1980). If the two-way ANOVA indicated an effect of time (number of days) on thickness or serum relaxin levels, the paired t-test was used to make pair-wise comparisons following a one-way ANOVA. Significant differences in implantation bleeding and placental size were determined using a Student's t-test (Zar J H, 1980). Significant differences in implantation and pregnancy rates were determined by Chi-square test, except for analysis of multiple pregnancy rates on Day 67, for which the Fisher exact test was used (Zar J H, 1980). Differences were considered significant when $p<0.05$.

Results

Donor Characteristics and Embryo Production

Donor female cycle interval (mense to mense) and duration of menses in the 3 cycles preceding the donor cycle were regular, with cycle intervals ranging from 31.3±0.7 days to 33.9±2.9 days and menses duration ranging from 2.9±0.2 days to 3.7±0.3 days. A total of 413 oocytes from ten females were aspirated, and 340 were classified as MII and suitable for use in IVF procedures. Of the MII oocytes inseminated, 222 fertilized (60+12%) and 212 fertilized embryos cleaved to the eight-cell stage within 48 hours of insemination (95+3%). Fertilization and cleavage rates, adjusted for failed fertilizations resulting from poor sperm quality, poor response of sperm to chemical hyper-activation, and/or poor oocyte quality (two of the ten superovulation cycles), were 80+8% and 95+4%, respectively.

Recipient Treatment and Embryo Transfer

Recipient cycle interval and duration in the three cycles preceding pump implantation were regular, with cycle intervals ranging from 29.4±0.8 days to 32.6±1.6 days and cycle duration ranging from 3.6±0.2 days to 3.6±0.3 days. Body weights of the recipients were similar at pump implantation (vehicle-treated group 2.65+0.31 kg; relaxin-treated group 2.81+0.36 kg) and at embryo transfer 7 days later (vehicle-treated group 2.67+0.35 kg; relaxin-treated group 2.77+0.32 kg).

Embryos transferred to relaxin- and vehicle-treated animals exhibited post-thawing cell survival rates of 90%±3.3% and 89%±3.1%, respectively. The first and second embryos transferred to the left and right oviducts of relaxin- and vehicle-treated animals did not differ significantly in their cell survival rates, with post-thawing cell survival rates ranging from 86.3%±6.2% to 97.7%±2.3%. All of the thawed embryos exhibiting 50% cell survival post-thawing (not suitable for transfer) developed to hatched-blastocysts (4/4, 100%) in culture. Embryos with less than 50% blastomere survival post-thawing failed to develop past the eight-cell stage (0/3, 0%).

Serum Hormone Analysis

None of the animals in either the vehicle- or relaxin-treated groups had detectable rhRLX levels on Day 0 prior to pump implantation. rhRLX was not detected in any of the vehicle-treated animals at any of the observation time points (Day 7, 21, 28, or 67). In the relaxin-treated group, 10/11 animals demonstrated circulating rhRLX levels at Day 7. The average Day 7 serum concentration in these animals was 1.2+0.37 ng/mL (n=10). The monkey that did not have detectable rhRLX levels on Day 7 failed to demonstrate rhRLX levels at any of the observation time points; therefore, this female was omitted from the relaxin-treated group and all of the analyses presented below. At Day 21, rhRLX levels in the relaxin group averaged 3.7+1.3 ng/mL (NS compared to Day 7). By Day 28 and 67, serum rhRLX concentrations had dropped to 0.20+0.10 ng/mL and 0.04+0.04 ng/mL, respectively (p=0.035 and 0.03 vs Day 21, respectively).

Endometrial Thickness and Embryo Implantation

Four endometrial thickness measurements were technically possible on all four sonograph days (Days 0, 7, 21, and 28) in seven females in the vehicle-treated group and nine females in the relaxin-treated group. A significant effect of treatment and time on endometrial thickness was found (p<0.0001 for interaction). Comparisons between mean thickness measurements in the vehicle (n=7) and treatment (n=9) groups at the observation time points indicated that mean thicknesses in the vehicle and relaxin groups on Day 7 were significantly different (p=0.01) (Table III). No significant time effect for vehicle controls was found (p=0.10), but a significant time effect for the relaxin group was evident (p<0.0001). In this group, endometrial thickness on Day 7 measured 0.32+0.02 cm, a significant increase in thickness from Day 0 (0.23+0.01 cm) (p=0.003). Whereas all nine females in the relaxin-treated group showed an increase in endometrial thickness from Day 0 to Day 7, five of the seven in the vehicle-treated group showed increases, one showed no change, and one showed a decrease in thickness (FIG. 1). The relaxin treatment-associated increase in thickness was transient, so that by Day 21, the difference was not significant and on Day 28, the difference was smaller, when compared to Day 0 (p=0.035).

Of the 44 embryos transferred to 11 vehicle-treated recipients, 13 implanted by Day 21, for an implantation rate of 29.5% in the vehicle group (Table IV). This was lower than the implantation rate of 42.5% (17/40 embryos) observed in the relaxin-treated group at Day 21. Implantation rates in the relaxin-treated group were also higher than that observed in the vehicle-treated group at Days 28 and 67. Overall pregnancy rates at Day 21 were high in both groups; i.e. 91% (10/11) in the vehicle-treated group and 80% (8/10) in the relaxin-treated group. Sustained pregnancy rates at Day 67 were 54.5% (6/11) in the vehicle-treated group and 50.0% (5/10) in the relaxin-treated group. Although there were initially three multiple pregnancies (three twin pregnancies) in the vehicle-treated group (3/9, 33%), there were none remaining at Day 67 (0/6, 0%). The number of multiple pregnancies in relaxin-treated animals (three twins, three triplets) was initially six (6/8, 75%), of which three remained at Day 67 (3/5, 60%; p=0.06 vs. vehicle-treated pregnancies at Day 67). Of these three remaining pregnancies, two were twin and one was a triplet pregnancy. Therefore, it is possible that relaxin increased blood flow to the uterus so that the growth of multiple fetuses could be sustained. In pregnant females in the vehicle-treated group (n=6), placental sign-associated bleeding started 19.7±2.3 days following embryo transfer and lasted an average of 9.8±2.6 days. In relaxin-treated pregnancies (n=5), implantation bleeding started 12±0.8 days after embryo transfer (p<0.02 vs. vehicle group) and lasted an average of 19.2±2.2 days (p<0.05 versus vehicle-treated pregnancies). Menses in non-pregnant females (n=4) in the vehicle-treated group occurred at day 20.0+3.8 following embryo transfer and lasted 3.3+0.3 days, with one additional female showing no evidence of menses. Menses initiated 16.2+1.5 days following embryo transfer in non-pregnant relaxin-treated females, and lasted for 4.0+0.3 days (n=5) (NS compared to vehicle-treated group).

At Day 67, assessment of placental surface area and circumferences by ultrasound was technically feasible in four of the six control pregnancies and in three of five relaxin-treated pregnancies. Fetal movement interfered with measurement in the other females. Placental surface area was 0.59+0.17 cm$^2$ and 0.87+0.18 cm$^2$ in the vehicle- and relaxin-treated groups, respectively. Placental circumference measured 2.73+0.68 cm and 3.37+0.33 cm in the vehicle- and relaxin-treated groups, respectively. Thus, increases in placental surface area and circumference were observed in the relaxin-treated subjects. The fact that recipient monkeys were presumably fertile at the outset of the study and may have exhibited normal levels of endogenous macaque relaxin were admittedly factors that could have biased the study toward not showing a more pronounced effect of exogenously provided relaxin on implantation, pregnancy rates, placental growth and other factors related to fetal growth.

Positive effects of infusion of relaxin on endometrial thickness were observed in this study. In humans, endometrial thickness increases progressively during a normal menstrual cycle from a nadir in the early proliferative phase to a maximum during the early/mid-luteal phase, remaining at this maximum until one to two days prior to menses. This increase is believed to reflect physiological alterations occurring in the tissue, including an increase in endometrial blood flow and glandular secretory and stromal predecidual changes that occur under the influence of the hormonal milieu. Thus, thickness measurements may be useful as a general descriptive feature of a normally developing endometrium, and, in fact, have been used to identify abnormally thin endometria, which, for whatever reason, have a high implantation failure rate following IVF. Our results demonstrate that infusion of exogenous relaxin had a statistically significant positive influence on the thickness of the endometrium in cynomolgus monkeys. The increase in thickness may be due to the concerted effects of relaxin on multiple cell types within the endometrium, as both glandular and stromal elements possess relaxin receptors.

Relaxin administration in cynomolgus monkeys was also associated with an increased placental sign, or implantation bleeding. Placental sign is a natural phenomenon which appears several days following mating in pregnant females in some non-human primate species. The bleeding is believed to be associated with embryonic implantation in monkeys and is, contrary to the situation in humans, a positive sign of pregnancy. Relaxin treatment was associated with a significantly shorter time period to first appearance of the placental sign and a significant increase in duration of implantation bleeding in *M. fascicularis*, compared to treatment with vehicle alone. Relaxin, therefore, likely has a positive influence on blood flow to the endometrium/placenta.

TABLE III

Serial endometrial thickness measurements in vehicle- and relaxin-treated recipient *M. fascicularis*.

| Treatment Group | Endometrial Thickness (cm) [a] | | | |
|---|---|---|---|---|
| | Day 0 | Day 7 | Day 21 | Day 28 |
| Vehicle | 0.23 ± 0.03 | 0.27 ± 0.02 | 0.27 ± 0.01 | 0.26 ± 0.02 |
| Relaxin | 0.23 ± 0.01 | 0.32 ± 0.02 [b, c] | 0.25 ± 0.02 | 0.27 ± 0.02 [d] |

[a] Each endometrial thickness measurement is the mean of two sagittal and two transverse measurements, and is expressed as mean ± SEM in vehicle- (n = 7) and relaxin-treated (n = 9) groups.
[b] p = 0.01 compared to Day 7 in the vehicle group, by t-test
[c] p = 0.003 compared to Day 0 in the relaxin-treated group, by paired t-test
[d] p = 0.035 compared to Day 0 in the relaxin-treated group, by paired t-test

EXAMPLE 3

A decrease in placental hepatocyte growth factor (HGF) expression has been associated with SGA, IUGR, and preeclampsia (Dokras et al., 2001, Biol Reprod 65:1278-1288; Kauma et al., J Clin Endocrinol Metab 84:4092-4096). HIF-1α is a known upregulator of VEGF expression, as well as other angiogenic cytokines, and is also involved in increasing expression of glucose transporter-1, which is involved in glucose uptake by the developing placenta. Relaxin upregulation of HIF-1α protein expression may make HIF-1α available for activation under hypoxic conditions.

The data in this Example show that relaxin induces molecules that are deficient in IUGR and preeclampsia. Specifically, the data show that (1) relaxin increases the expression of HGF in endometrial stromal cells, as detected by quantitative PCR and ELISA; and (2) relaxin increases expression of HIF-1α in endometrial stromal cells under normoxic conditions.

Figure 2:
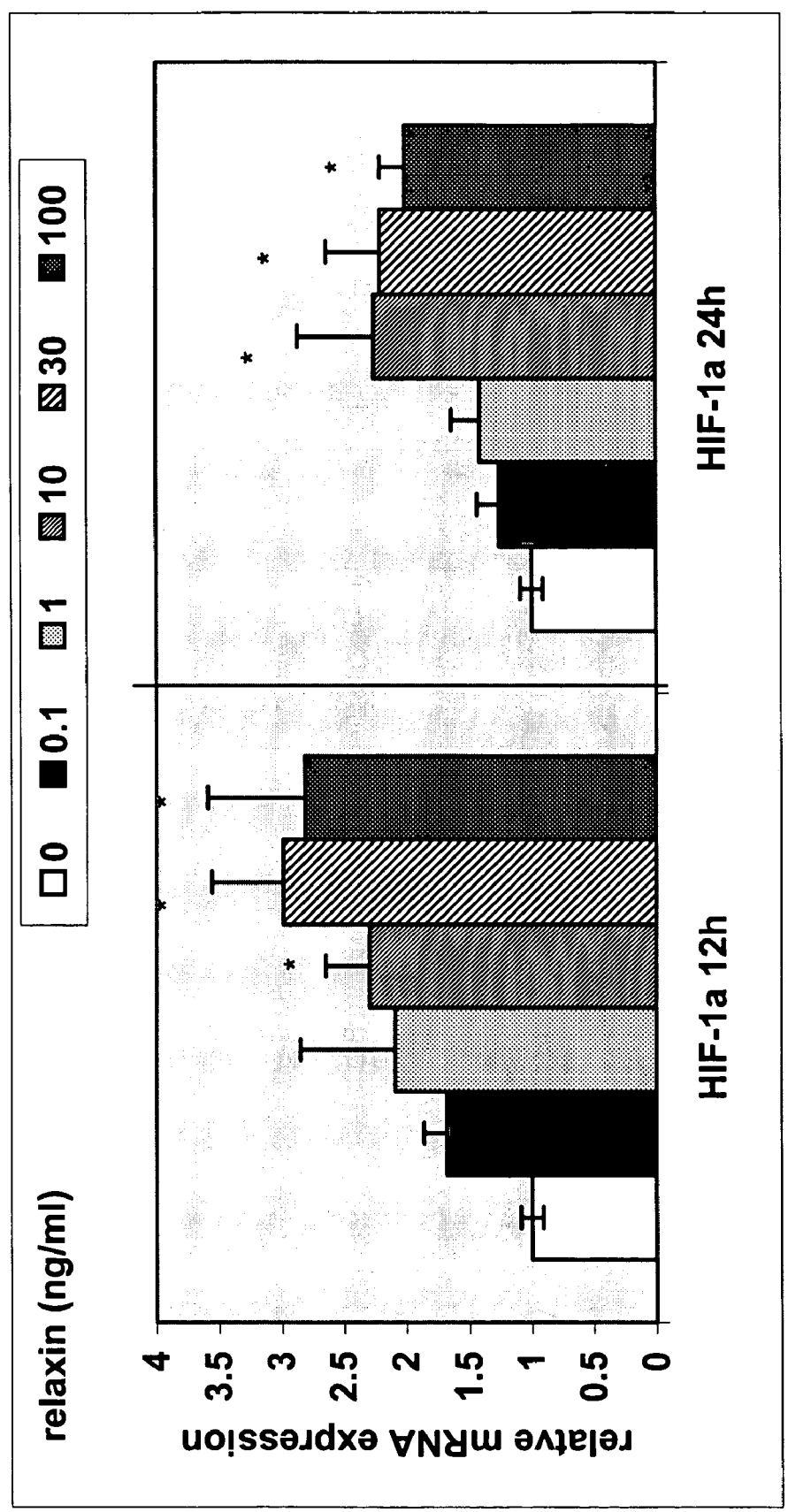
FIG. 2 shows the results of real-time quantitative RT-PCR determination of abundance of HIF-1α transcripts in NHE cells 12 hours and 24 hours after treatment. A rhRLX dose dependent (0.1-100 ng/mL) increase in HIF-1α mRNA is observed. Data shown represent means±SD; n=3 independent tissue culture experiments; *p<0.05, compared to untreated control, by Bonferroni t-test.

Real-time quantitative RT-PCR determination of abundance of HIF-1α transcripts in NHE cells. NHE cells were treated with vehicle or rhRLX (0.1-100 ng/ml) for 12 h and 24 h. Total RNA was isolated and expression of HIF 1α transcripts were quantified and normalized to 18S RNA. The level of HIF-1α/18S expression in control cultures was expressed as 1.0. rhRLX caused a dose-dependent significant upregulation of HIF 1α transcripts compared to untreated control (FIG. 2).

Figure 3:
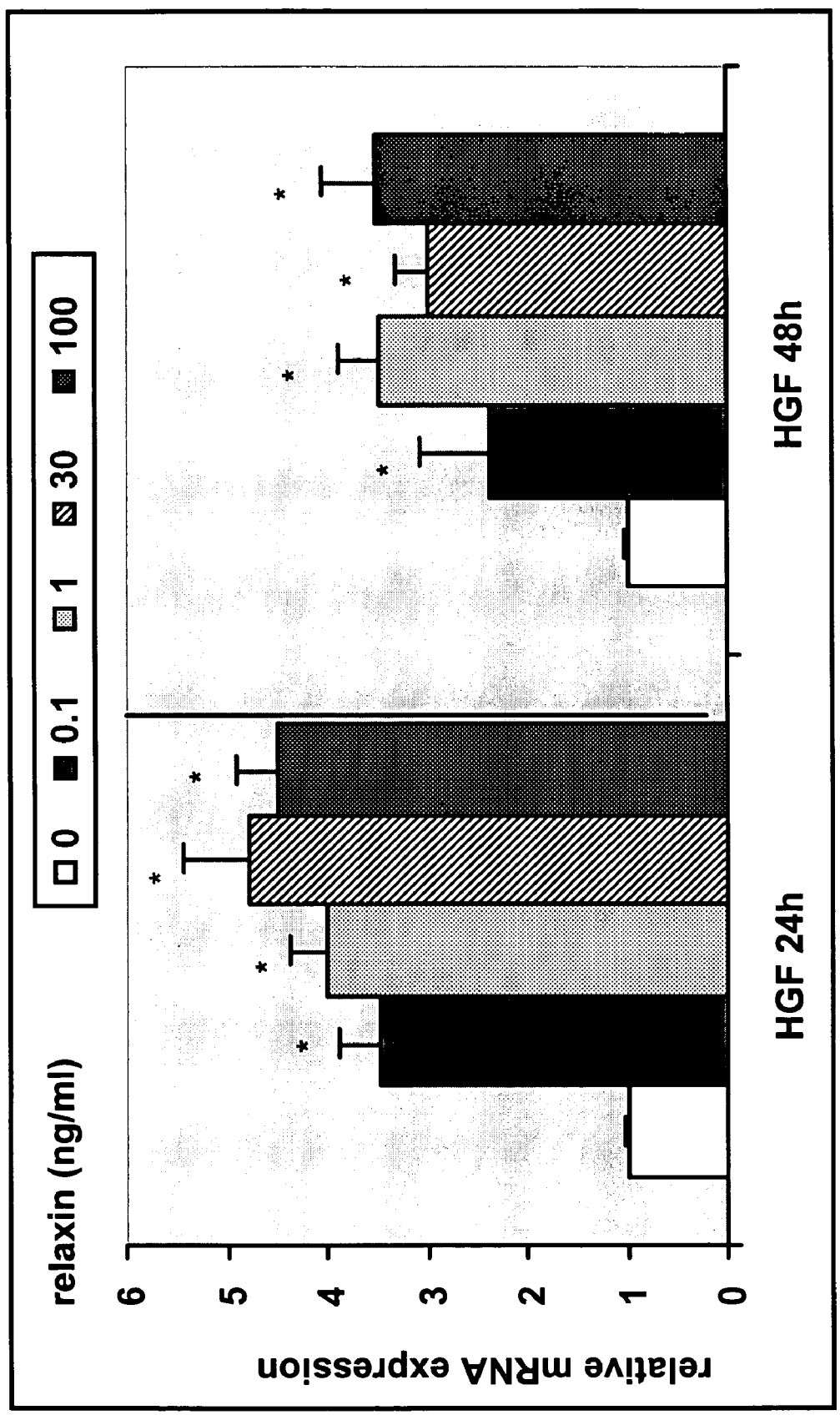
FIG. 3 shows the results of real time quantitative RT-PCR determination of abundance of transcripts of HGF in NHE cells 24 and 48 hours after treatment. A rhRLX dose dependent (0.1-100 ng/mL) increase in HGF mRNA is observed. Data shown represent means±SD; n=3 independent tissue culture experiments; *p<0.05, compared to untreated control, by Bonferroni t-test.

Real time quantitative RT-PCR determination of abundance of transcripts of HGF in NHE cells. NHE cells were treated with vehicle or rhRLX (0.1-100 ng/ml) for 24 h and 48 h. Total RNA was isolated and expression of HGF transcripts were quantified and normalized to the housekeeping gene, GAPDH. The level of HGF/GAPDH expression in control cultures was expressed as 1.0. rhRLX caused a 4-fold significant upregulation of HGF transcripts compared to untreated control at 24 h. A 2- to 3-fold induction of the transcripts was seen at 48 h (see FIG. 3).

Figure 4:
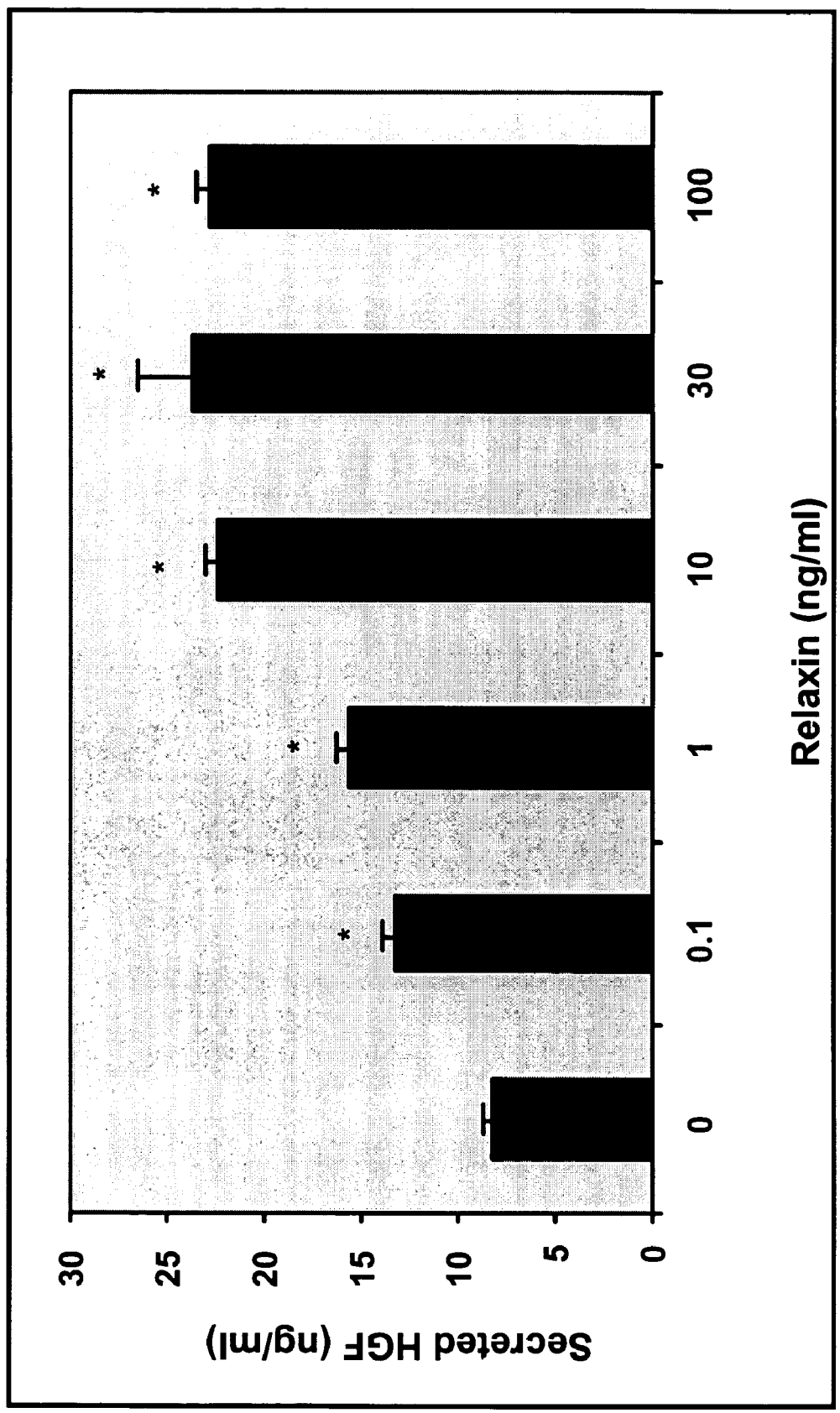
FIG. 4 shows the stimulation by rhRLX of secreted HGF protein in NHE cells by rhRLX. A rhRLX dose dependent (0.1-100 ng/mL) increase in HGF protein is observed. Data shown represent means±SD; n=3 independent experiments; *p<0.05, compared to untreated control, by Bonferroni t-test.

Stimulation of secreted HGF protein in NHE cells by rhRLX. HGF protein was quantified in the conditioned media 24 h following rhRLX treatment (0.1-100 ng/ml) using a commercially available ELISA kit. rhRLX induced a dose-dependent upregulation of HGF protein (see FIG. 4).

All patents and publications mentioned in the specifications are indicative of the levels of those skilled in the art to which the invention pertains. All patents and publications are herein incorporated by reference to the same extent as if each

TABLE IV

Implantation and pregnancy rates in vehicle- and relaxin-treated *M. fascicularis*

| Treatment Group | Implantation Rate (%) | | | Pregnancy Rate (%) | | | Multiple pregnancy rate (%) | | |
|---|---|---|---|---|---|---|---|---|---|
| | Day 21 | Day 28 | Day 67 | Day 21 | Day 28 | Day 67 | Day 21 | Day 28 | Day 67 |
| Vehicle | 29.5 | 27.2 | 13.6 | 90.0 | 81.8 | 54.5 | 30.0 | 33.0 | 0.0 |
| (n) [a] | (44) | (44) | (44) | (11) | (11) | (11) | (10) | (9) | (6) |
| Relaxin | 42.5 | 40.0 | 25.0 | 80.0 | 70.0 | 50.0 | 66.7 | 62.5 | 60.0 [b] |
| (n) | (40) | (40) | (40) | (10) | (10) | (10) | (9) | (8) | (5) |

[a] n = number of embryos transferred in implantation rate category, number of females in pregnancy rate and multiple pregnancy rate categories
[b] p = 0.06 versus multiple pregnancy rate at Day 67 in vehicle-treated females, by the Fisher exact test (one-tailed)

What is claimed is:

1. A method of increasing intrauterine fetal growth rate, the method comprising administering to a primate in need thereof a therapeutically effective amount of relaxin sufficient to maintain a serum concentration of at least about 1-2 ng/mL in said primate in order to increase fetal growth rate, wherein said relaxin is administered parenterally or by continuous subcutaneous infusion during the first trimester of pregnancy.

2. The method of claim 1 wherein the relaxin is further administered before and after ovulation.

3. The method of claim 1 wherein the relaxin is further administered for about a week before ovulation.

4. The method of claim 1 wherein the relaxin is administered in an amount sufficient to result in the birth of a baby of at least around normal birth weight.

5. The method of claim 1 wherein the relaxin is administered in an amount sufficient to maintain a serum concentration of at least around 1 ng/mL.

6. The method of claim 1 wherein the relaxin is administered parenterally.

7. The method of claim 1 wherein the relaxin is administered by continuous subcutaneous infusion.

8. The method of claim 7 wherein the relaxin is administered at a dose between 10 µg/kg/day and 200 µg/kg/day.

9. The method of claim 1 wherein the increase in fetal growth rate is assessed by an imaging technique.

10. The method of claim 9 wherein the imaging technique is chosen from the group consisting of ultrasonic imaging and magnetic resonance imaging.

11. The method of claim 1 wherein the pregnant primate is diagnosed as hosting a fetus with intrauterine growth retardation.

12. The method of claim 11 wherein the diagnosis is by an imaging technique.

13. The method of claim 12 wherein the imaging technique is chosen from the group consisting of ultrasonic imaging and magnetic resonance imaging.

14. The method of claim 1 wherein the pregnant primate has a condition that increases the risk of fetal intrauterine growth retardation.

15. The method of claim 14, wherein the condition is selected from the group consisting of lupus, hyperthyroidism, hypertension, preeclampsia, malarial infection, serum antiphospholipid antibodies, a history of recent spontaneous abortion, a history of intrauterine growth retardation, a history of having children with low birthweight, a multiple gestation pregnancy, and a pregnancy resulting from in vitro fertilization and embryo transfer.

16. The method of claim 1 wherein the primate is a human.

17. The method of claim 1 wherein the primate is a non-human primate.

* * * * *